(12) United States Patent
Adler et al.

(10) Patent No.: US 12,042,433 B2
(45) Date of Patent: Jul. 23, 2024

(54) SYSTEMS AND METHODS FOR EYE TRACKING DURING EYE TREATMENT

(71) Applicant: Avedro, Inc., Waltham, MA (US)

(72) Inventors: Desmond Christopher Adler, Bedford, MA (US); David Usher, Waltham, MA (US); Mikhail Smirnov, North Andover, MA (US)

(73) Assignee: Avedro, Inc., Waltham, MA (US)

( * ) Notice: Subject to any disclaimer, the term of this patent is extended or adjusted under 35 U.S.C. 154(b) by 912 days.

(21) Appl. No.: 16/978,694

(22) PCT Filed: Mar. 5, 2019

(86) PCT No.: PCT/US2019/020839
§ 371 (c)(1),
(2) Date: Sep. 5, 2020

(87) PCT Pub. No.: WO2019/173403
PCT Pub. Date: Sep. 12, 2019

(65) Prior Publication Data
US 2020/0397613 A1    Dec. 24, 2020

Related U.S. Application Data

(60) Provisional application No. 62/638,621, filed on Mar. 5, 2018.

(51) Int. Cl.
*A61F 9/007* (2006.01)
*A61F 9/00* (2006.01)

(52) U.S. Cl.
CPC .......... *A61F 9/0079* (2013.01); *A61F 9/0008* (2013.01)

(58) Field of Classification Search
CPC .... A61F 9/0079; A61F 9/008; A61F 9/00821; A61F 2009/00893; A61N 5/062; A61N 2005/0626; A61N 5/067

(Continued)

(56) References Cited

U.S. PATENT DOCUMENTS

| | | |
|---|---|---|
| 4,034,750 A | 7/1977 | Seiderman |
| 4,665,913 A | 5/1987 | L'Esperance, Jr. |

(Continued)

FOREIGN PATENT DOCUMENTS

| | | |
|---|---|---|
| DE | 102008046834 | 3/2010 |
| EP | 1561440 | 8/2005 |

(Continued)

OTHER PUBLICATIONS

Office Action for CN Patent Application No. 2020-546332 dated Mar. 20, 2023.

(Continued)

*Primary Examiner* — Ahmed M Farah
(74) *Attorney, Agent, or Firm* — K&L Gates LLP

(57) ABSTRACT

A corneal cross-linking system includes a light source configured to emit a photoactivating light. The system includes a spatial light modulator configured to receive the photoactivating light from the light source and provide a pixelated illumination. The spatial light modulator defines a maximum area for the pixelated illumination. The system includes a controller configured to cause the spatial light modulator to project a first pixelated illumination onto the cornea to photoactivate a cross-linking agent applied to a treatment area. The first pixelated illumination has an area that is smaller than the maximum area defined by the spatial light modulator. The controller is configured to determine movement of the cornea. In response to the movement, the controller controls the spatial light modulator to project a second pixelated illumination to the treatment area based on a translation and/or transformation of the first pixelated illumination to continue photoactivating the cross-linking agent.

10 Claims, 35 Drawing Sheets

(58) Field of Classification Search
USPC .................................. 606/4, 10–12, 17, 18
See application file for complete search history.

(56) References Cited

U.S. PATENT DOCUMENTS

| | | |
|---|---|---|
| 4,712,543 A | 12/1987 | Baron |
| 4,764,007 A | 8/1988 | Task |
| 4,891,043 A | 1/1990 | Zelmer et al. |
| 4,969,912 A | 11/1990 | Kelman et al. |
| 4,994,058 A | 2/1991 | Raven et al. |
| 5,019,074 A | 5/1991 | Muller |
| 5,171,318 A | 12/1992 | Gibson et al. |
| 5,281,211 A | 1/1994 | Parel et al. |
| 5,332,802 A | 7/1994 | Kelman et al. |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,624,437 A | 4/1997 | Freeman et al. |
| 5,779,696 A | 7/1998 | Berry et al. |
| 5,786,893 A | 7/1998 | Fink et al. |
| 5,891,131 A | 4/1999 | Rajan et al. |
| 5,910,110 A | 6/1999 | Bastable |
| 6,033,396 A | 3/2000 | Huang et al. |
| 6,139,876 A | 10/2000 | Kolta |
| 6,161,544 A | 12/2000 | DeVore et al. |
| 6,188,500 B1 | 2/2001 | Rudeen et al. |
| 6,218,360 B1 | 4/2001 | Cintron et al. |
| 6,270,221 B1 | 8/2001 | Liang et al. |
| 6,280,436 B1 | 8/2001 | Freeman et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,394,999 B1 | 5/2002 | Williams et al. |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,617,963 B1 | 9/2003 | Watters et al. |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,331,350 B2 | 2/2008 | Kochevar et al. |
| 7,402,562 B2 | 7/2008 | DeWoolfson et al. |
| 7,731,362 B2 | 6/2010 | Gerlach |
| 7,753,943 B2 | 7/2010 | Strong |
| 7,898,656 B2 | 3/2011 | Yun et al. |
| 7,935,058 B2 | 5/2011 | Dupps et al. |
| 8,111,394 B1 | 2/2012 | Borysow et al. |
| 8,115,919 B2 | 2/2012 | Yun et al. |
| 8,366,689 B2 | 2/2013 | Marshall et al. |
| 8,414,911 B2 | 4/2013 | Mattson et al. |
| 8,475,437 B2 | 7/2013 | Mrochen et al. |
| 11,642,244 B2 * | 5/2023 | Adler ..................... A61F 9/008 606/5 |
| 2001/0055095 A1 | 12/2001 | D'Souza et al. |
| 2002/0013577 A1 | 1/2002 | Frey et al. |
| 2002/0159618 A1 | 10/2002 | Freeman et al. |
| 2002/0164379 A1 | 11/2002 | Nishihara et al. |
| 2003/0175259 A1 | 9/2003 | Karageozian et al. |
| 2003/0189689 A1 | 10/2003 | Rathjen |
| 2003/0231285 A1 | 12/2003 | Ferguson |
| 2004/0002694 A1 | 1/2004 | Pawlowski et al. |
| 2004/0093046 A1 | 5/2004 | Sand |
| 2004/0199079 A1 | 10/2004 | Chuck et al. |
| 2005/0038471 A1 | 2/2005 | Chan et al. |
| 2005/0096515 A1 | 5/2005 | Geng |
| 2005/0149006 A1 | 7/2005 | Peyman |
| 2005/0271590 A1 | 12/2005 | Schwartz et al. |
| 2006/0135957 A1 | 6/2006 | Panescu |
| 2006/0149343 A1 | 7/2006 | Altshuler et al. |
| 2006/0195076 A1 | 8/2006 | Blumenkranz et al. |
| 2006/0276777 A1 | 12/2006 | Coroneo |
| 2007/0024860 A1 | 2/2007 | Tobiason et al. |
| 2007/0048340 A1 | 3/2007 | Bran et al. |
| 2007/0123845 A1 | 5/2007 | Lubatschowski |
| 2007/0135805 A1 | 6/2007 | Peyman |
| 2007/0142828 A1 | 6/2007 | Peyman |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0063627 A1 | 3/2008 | Stucke et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0116096 A1 | 5/2009 | Zalevsky et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0234335 A1 | 9/2009 | Yee |
| 2009/0275929 A1 | 11/2009 | Zickler |
| 2010/0028407 A1 | 2/2010 | Del Priore et al. |
| 2010/0057060 A1 | 3/2010 | Herekar |
| 2010/0069894 A1 | 3/2010 | Mrochen et al. |
| 2010/0082018 A1 | 4/2010 | Panthakey et al. |
| 2010/0094197 A1 | 4/2010 | Marshall et al. |
| 2010/0114109 A1 | 5/2010 | Peyman |
| 2010/0149487 A1 | 6/2010 | Ribak |
| 2010/0173019 A1 | 7/2010 | Paik et al. |
| 2010/0189817 A1 | 7/2010 | Krueger et al. |
| 2010/0204584 A1 | 8/2010 | Omberg et al. |
| 2010/0210996 A1 | 8/2010 | Peyman |
| 2010/0318017 A1 | 12/2010 | Lewis et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0152219 A1 | 6/2011 | Stagni et al. |
| 2011/0190742 A1 | 8/2011 | Anisimov |
| 2011/0202114 A1 | 8/2011 | Kessel et al. |
| 2011/0208300 A1 | 8/2011 | Eugene et al. |
| 2011/0237999 A1 | 9/2011 | Muller et al. |
| 2011/0264082 A1 | 10/2011 | Mrochen |
| 2011/0288466 A1 | 11/2011 | Muller et al. |
| 2011/0301524 A1 | 12/2011 | Bueler et al. |
| 2012/0083772 A1 | 4/2012 | Rubinfield et al. |
| 2012/0203161 A1 | 8/2012 | Herekar |
| 2012/0215155 A1 | 8/2012 | Muller et al. |
| 2012/0289886 A1 | 11/2012 | Muller et al. |
| 2012/0302862 A1 | 11/2012 | Yun et al. |
| 2012/0303008 A1 | 11/2012 | Muller et al. |
| 2012/0310083 A1 | 12/2012 | Friedman et al. |
| 2012/0310223 A1 | 12/2012 | Knox et al. |
| 2013/0060187 A1 | 3/2013 | Friedman et al. |
| 2013/0085370 A1 | 4/2013 | Friedman et al. |
| 2013/0116757 A1 | 5/2013 | Russmann |
| 2014/0194957 A1 | 7/2014 | Rubinfield et al. |
| 2014/0249509 A1 | 9/2014 | Rubinfield et al. |
| 2017/0184717 A1 | 6/2017 | Feigin |
| 2018/0206719 A1 * | 7/2018 | Adler ..................... A61B 3/14 |
| 2021/0000646 A1 * | 1/2021 | Adler ..................... A61F 9/0079 |

FOREIGN PATENT DOCUMENTS

| | | |
|---|---|---|
| EP | 1790383 | 5/2007 |
| IT | MI2010A001236 | 5/2010 |
| JP | 2013-52988 A | 6/2013 |
| KG | 1376 | 8/2011 |
| RU | 2086215 | 8/1997 |
| RU | 2420330 | 6/2011 |
| RU | 2456971 | 7/2012 |
| WO | 2000074648 | 12/2000 |
| WO | 2001058495 | 8/2001 |
| WO | 2005110397 | 11/2005 |
| WO | 2006012947 | 2/2006 |
| WO | 2006128038 | 11/2006 |
| WO | 2007001926 | 1/2007 |
| WO | 2007053826 | 5/2007 |
| WO | 2007120457 | 10/2007 |
| WO | 2007139927 | 12/2007 |
| WO | 2007143111 | 12/2007 |
| WO | 2008000478 | 1/2008 |

(56) References Cited

FOREIGN PATENT DOCUMENTS

| | | |
|---|---|---|
| WO | 2008052081 | 5/2008 |
| WO | 2008095075 | 8/2008 |
| WO | 2009073213 | 6/2009 |
| WO | 2009114513 | 9/2009 |
| WO | 2009146151 | 12/2009 |
| WO | 2010011119 | 1/2010 |
| WO | 2010015255 | 2/2010 |
| WO | 2010023705 | 3/2010 |
| WO | 2010093908 | 8/2010 |
| WO | 2011019940 | 2/2011 |
| WO | 2011116306 | 9/2011 |
| WO | 2011116306 A2 | 9/2011 |
| WO | 2012004726 | 1/2012 |
| WO | 2012149570 | 11/2012 |
| WO | 2012174453 | 12/2012 |
| WO | 2013148713 | 10/2013 |
| WO | 2013148895 | 10/2013 |
| WO | 2013148896 | 10/2013 |
| WO | 2013149075 | 10/2013 |
| WO | 2014202736 | 12/2014 |
| WO | 2015062648 A1 | 5/2015 |
| WO | 2017184717 A1 | 10/2017 |
| WO | WO-2017184717 A1 * | 10/2017 |

OTHER PUBLICATIONS

1 Office Action for related Chinese Application No. 201980030236.0; action dated Oct. 27, 2022; (17 pages).
Extended European search report mailed Nov. 24, 2023 in related EP 23195723.4.
Rocha K., et al., "Comparative Study of Riboflavin-UVA Crosslinking and "Flash-linking" Using Surface Wave Elastometry," Journal of Refractive Surgery, vol. 24 Issue 7, pp. S748-S751; Sep. 2008 (4 pages).
Rolandi et al. Correlation of Collagen-Linked Fluorescence and Tendon Fiber Breaking Time. Gerontology 1991;27 :240-243 (4 pages).
Scarcelli, G. et al., "Brillouin Optical Microscopy for Corneal Biomechanics", Investigative Ophthalmology & Visual Science, Jan. 2012, vol. 53, No. 1, pp. 185-190 (6 pages).
Sheehan M., et al., "Illumination System for Corneal Collagen Crosslinking," Optometry and Vision Science, vol. 88, No. 4, pp. 512-524; Apr. 2011 (13 pages).
Spoerl E. et al., "Safety of UVA-Riboflavin Cross-Linking of the Cornea," Cornea, vol. 26, No. 4, pp. 385-389; May 2007 (5 pages).
Spoerl E., et al., "Artificial Stiffening of the Cornea by Induction of Intrastromal Cross-links," Oer Ophthalmologe, vol. 94, No. 12, pp. 902-906; Dec. 1997 (5 pages).
Spoerl E., et al., "Induction of Cross-links in Corneal Tissue," Experimental Eye Research, vol. 66, Issue 1, pp. 97-103; Jan. 1998 (7 pages).
Spoerl E., et al., "Techniques for Stiffening the Cornea," Journal of Refractive Surgery, vol. 15, Issue 6, pp. 711-713; Nov.-Dec. 1999 (4 pages).
Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).
Thorton, I. et al., "Biomechancial Effects of Intraocular Pressure Elevation on Optic Berve/Lamina Cribrosa before and after Peripapillary Scleral Collagen Cross-Linking." Invest. Ophthalmol. Vis. Sci., Mar. 2009, 50(3): pp. 1227-1233.
UV-X: Radiation System for Treatment of Keratokonus, PESCHKE Meditrade GmbH; retrieved from http://www.peschkemed.ch/ on Sep. 27, 2011 (1 page) (date unknown, prior to Sep. 16, 2008).
Vasan S., et al., "An agent cleaving glucose-derived protein crosslinks in vitro and in vivo;" Letters to Nature, vol. 382, pp. 275-278; Jul. 18, 1996 (4 pages).
Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).

Wollensak G., "Crosslinking Treatment of Progressive Keratoconus: New Hope," Current Opinion in Ophthalmology, vol. 17(4), pp. 356-360; Aug. 2006 (5 pages).
Wollensak G., et al., "Biomechanical and Histological Changes After Corneal Crosslinking With and Without Epithelial Debridement," J. Cataract Refract. Surg., vol. 35, Issue 3, pp. 540-546; Mar. 2009 (7 pages).
Wollensak G., et al., "Collagen Crosslinking of Human and Porcine Sclera," J. Cataract Refract. Surg., vol. 30, Issue 3, pp. 689-695; Mar. 2004 (7 pages).
Wollensak G., et al., "Cross-linking of Scleral Collagen in the Rabbit Using Riboflavin and UVA," Acta Ophtalmologica Scandinavica, vol. 83(4), pp. 477-482; Aug. 2005 (6 pages).
Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).
Wollensak G., et al., "Riboflavin/Ultraviolet-A-induced Collagen Crosslinking for the Treatment of Keratoconus," American Journal of Ophthalmology, vol. 135, No. 5, pp. 620-627; May 2003 (8 pages).
Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. Vol. 29, No. 9, Sep. 2003 (pp. 1780-1785).
Wong, J. et al., "Post-Lasik ectasia: PRK following previous stablization and effective management with Riboflavin I ultraviolet A-induced collagen cross-linking," Association for Research in Vision and Ophthalmology, 2006 (1 page).
Yang H., et al., "3-D Histomorphometry of the Normal and Early Glaucomatous Monkey Optic Nerve Head: Lamina Cribrosa and Peripapillary Scleral Position and Thickness," Investigative Ophthalmology & Visual Science, vol. 48, No. 10, pp. 4597-4607; Oct. 2007 (11 pages).
Yang N., Oster G. Dye-sensitized photopolymerization in the presence of reversible oxygen carriers. J. Phys. Chem. 74, 856-860 (1970).
Zhang, Y. et al., "Effects of Ultraviolet-A and Riboflavin on the Interaction of Collagen and Proteoglycans during Corneal Crosslinking", Journal of Biological Chemistry, vol. 286, No. 15, dated Apr. 5, 2011 (pp. 13011-13022).
International Patent Application No. PCT/US2019/020839, International Search Report, Aug. 9, 2019 (6 pages).
International Patent Application No. PCT/US2019/020839, Written Opinion of the ISA, Aug. 9, 2019 (9 pages).
Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164 (6 pages).
Averianova, O. S., "Nastoyaschee I buduschee kross-linkage." Mir Ofalmologii, 2010, [online] [retrieved on Feb. 13, 2014] Retrieved from the internet: http:/ /miroft.org.ualpublications/.html.
Baier J. et al., "Singlet Oxygen Generation by UVA Light Exposure of Endogenous Photosensitizers," Biophysical Journal, vol. 91(4), pp. 1452-1459; Aug. 15, 2006 (8 pages).
Ballou, D. et al., "Direct Demonstration Of Superoxide Anion Production During The Oxidation Of Reduced Flavin And Of Its Catalytic Decomposition By Erythrocuprein," Biochemical And Biophysical Research Communications vol. 36, No. 6, pp. 898-904, Jul. 11, 1969 (7 pages).
Barbarino, S. et al., "Post-LASIK ectasia: Stabilization and Effective Managmeent with Riboflavin / ultraviolet A-induced collagen cross-linking," Association for Research in Vision and Ophthalmology, 2006 (1 page).
Bruel, A., "Changes In Biomechanical Properties, Composition Of Collagen And Elastin, And Advanced Glycation Endproducts Of The Rat Aorta In Relation To Age," Atherosclerosis 127, Mar. 14, 1996 (11 pages).
Chace, K.V. et al., Abstract for "The role of nonenzymatic glycosylation, transition metals, and free radicals in the formation of collagen aggregates", Arch Biochem Biophys., Aug. 1, 1991, 288(2) pp. 473-480 (1 page).

(56) References Cited

OTHER PUBLICATIONS

Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238 (8 pages).
Chan B.P., et al., "Effects of photochemical crosslinking on the microstructure of collagen and a feasibility study on controlled protein release;" Acta Biomaterialia, vol. 4, Issue 6, pp. 1627-1636; Jul. 1, 2008 (10 pages).
Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011 (3 pages).
Coskensevim E. et al., "Comparative Study of Corneal Collagen Cross-linking With Riboflaving and UVA Irradiation in Patients With Keratoconus," Journal of Refractive Surgery, vol. 25, issue 4, pp. 371-376; Apr. 2009 (6 pages).
Erskine H., "Avedro Becomes Sponsor of US FDA Clinical Trials of Corneal Collagen Crosslinking," Press Release, Mar. 16, 2010 (1 page).
Fite et al. Noninvasive Multimodal Evaluation of Bioengineered Cartilage Constructs Combining Time-Resolved Fluorescence and Ultrasound Imaging. Tissue Eng: Part C vol. 17, No. 4, 2011 (10 pages).
Friedman, M. et al. "Advanced Corneal Cross-Linking System with Fluorescence Dosimetry", Journal of Ophthalmology, vol. 2012, Article ID 303459, dated May 7, 2012 (6 pages).
Gibson, Q. et al., "The Oxidation Of Reduced Flavin Mononucleotide By Molecular Oxygen," Biochem. J. (1962) 83, 368-377 (10 pages).
Givens et al. "A Photoactivated Diazpryruvoyl Cross-Linking Agent for Bonding Tissue Containing Type-I Collagen." Photochemistry and Photobiology. Vol. 78, No. 1, 2003 (pp. 23-29).
Glenn J.V., et al., "Advanced Glycation End Product (AGE) Accumulation on Bruch's Membrane: Links to Age-Related RPE Dysfunction;" Investigative Ophthalmology & Visual Science, vol. 50, No. 1, pp. 441-451; Jan. 2009 (11 pages).
Hafezi F., et al., "Collagen Crosslinking with Ultraviolet-A and Hypoosmolar Riboflavin Solution in Thin Corneas," J. Catract Refract. Surg., vol. 35, No. 1, pp. 621-624; Apr. 2009 (4 pages).
Hitzenberger et al., "Birefringence Properties Of The Human Cornea Measured With Polarization Sensitive Optical Coherence Tomography," Bull. Soc. Beige Ophtalmol., 302, 153-168, 2006.
Holmstrom, B. et al., "Riboflavin As An Electron Donor In Photochemical Reactions," 1867-1871, Nov. 29, 1960 (5 pages).
IMEX, "KXL System: Crosslinking Para Cirugia Corneal Bibliografia Cientifica," Product Literature, Nov. 23, 2010 (24 pages).
Kamaev et al., "Photochemical Kinetics Of Corneal Cross-Linking With Riboflavin," Investigative Ophthalmology & Visual Science, Apr. 2012, vol. 53, No. 4, pp. 2360-2367 (8 pages).
Kampik D. et al., "Influence of Corneal Collagen Crosslinking With Riboflavin and Ultraviolet-A Irradiation on Excimer Laser Surgery," Investigative Opthalmology & Visual Science, vol. 51, No. 8, pp. 3929-3934; Aug. 2010 (6 pages).
Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.
Kanellopoulos, A. J., "Keratoconus management: UV A-induced collagen cross-linking followed by a limited topo-guided surface excimer ablation," American Academy of Ophthalmology, 2006 (25 pages).
Kanellopoulos, A. J., "Ultraviolet A cornea collagen cross-linking, as a pre-treatment for surface excimer ablation in the management of keratoconus and post-LASIK ectasia," American Academy of Ophthalmology, 2005 (28 pages).
Kissner Anja, et al., "Pharmacological Modification of the Epithelial Permeability by Benzalkonium Chloride in UVNRiboflavin Corneal Collagen Cross-Linking," Current Eye Research 35(8), pp. 715-721; Mar. 2010 (7 pages).
Koller T., et al., "Therapeutische Quervernetzung der Hornhaut mittels UVA und Riboflavin: Therapeutic Cross-Linking of the Cornea Using Riboflavin/UVA," Klinische Monatsblatter fur Augenheilkunde, val. 224, No. 9, pp. 700-706; Sep. 2007 (7 pages).
Koller, T. et. al., "Complication and failure rates after corneal crosslinking," Journal Cataract and refractive surgery, vol. 35, No. 8, Aug. 2009, pp. 1358-1362.
Kornilovsky, I. M. "Novye neinvazivnye tekhnologii lazernoy modifikatsii optiko-refraksionnykk struktur glaza. Refraktsionnaya khirurgiya I oftalmologiya." vol. 9, No. 3, 2006 (pts. 17-26).
Krueger Ronald R., "Rapid VS Standard Collagen CXL with Equivalent Energy Dosing," presentation slides, (26 pages); available at http://www.slideshare.net/logen/krueger-kerekar-rapid-cross-linking (date unknown, prior to Nov. 9, 2009).
Li, C. et al. "Elastic Properties of Soft Tissue-Mimicking Phantoms Assessed by Combined Use of Laser Ultrasonics and Low Coherence Interferometry." Optics Express. Vol. 19, No. 11, May 9, 2011 (pp. 10153-10163).
Li, C. et al. "Noncontact All-Optical Measurement of Corneal Elasticity." Optics Letters. Vol. 37, No. 10, May 15, 2012 (pp. 1625-1627).
Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).
Marzouky, et. al., Tensioactive-mediated Transepithelial Corneal Cross-linking—First Laboratory Report, European Ophthalmic Review, 2009, 3(2), pp. 67-70.
Massey, V., "Activation Of Molecular Oxygen By Flavins And Flavoproteins," The Journal of Biological Chemistry vol. 269, No. 36, Issue of September 9, pp. 22459-22462, 1994 (4 pages).
Meek, K.M. et al. "The Cornea and Sclera", Collagen: Structure and Mechanics, Chapter 13, pp. 359-396, 2008 (38 pages).
Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).
Muller L., et al., "The Specific Architecture of the Anterior Stroma Accounts for Maintenance of Corneal Curvature," Br. J. Opthalmol., vol. 85, pp. 437-443; Apr. 2001 (8 pages).
Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).
O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).
Pinelli R., et al., "C3-Riboflaving Treatments: Where Did We Come From? Where Are We Now?" Cataract & Refractive Surgery Today Europe, Summer 2007, pp. 36-46; Jun. 2007 (10 pages).
Pinelli, R. "Corneal Cross-Linking with Riboflavin: Entering a New Era in Ophthalmology." Ophthalmology Times Europe. vol. 2, No. 7, Sep. 1, 2006 (3 pages).
Pinelli, R., "Panel Discussion: Epithelium On/Off, Corneal abrasion for CCL contra", presented at the 3° International Congress of Corneal Cross Linking on Dec. 7-8, 2007 in Zurich (36 pages).
Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," J. Cataract Refract. Surgery, vol. 35, No. 6, pp. 1055-1062; Jun. 2009 (8 pages).
Proano C.E., et al., "Photochemical Keratodesmos for Bonding Corneal Incisions;" Investigative Ophthalmology & Visual Science, vol. 45, No. 7, pp. 2177-2181; Jul. 2004 (5 pages).
Randall, J. et al., "The Measurement and Intrepretation of Brillouin Scattering in the Lens of the Eye," The Royal Society, Abstract only, published 2013 [available online at http://rspb.royalsocietypublishing.org/content/214/11971449.short] (1 page).
Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].
Reiss, S. et al., "Non-Invasive, ortsaufgeloeste Bestimmung von Gewebeeigenschaften der Augenlinse, Dichte und Proteinkonzentra-

(56) References Cited

OTHER PUBLICATIONS tion unter Anwendung der Brillouin-spektroskopie", Klin Monatsbl Augenheilkd, vol. 228, No. 12, pp. 1079-1085, Dec. 13, 2011 (7 pages).
Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).

* cited by examiner

SYSTEMS AND METHODS FOR EYE TRACKING DURING EYE TREATMENT

CROSS REFERENCE TO RELATED APPLICATIONS

This application is a National Stage Application of International Patent Application No. PCT/US2019/020839, filed Mar. 5, 2019, which claims priority to and the benefit of U.S. Provisional Application No. 62/638,621, filed Mar. 5, 2018, the contents of these applications being incorporated entirely herein by reference.

BACKGROUND

Field

The present disclosure pertains to systems and methods for eye treatments, and more particularly, to systems and methods that track eye movement to deliver treatment to desired areas of the eye.

Description of Related Art

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

Cross-linking treatments may also be employed after surgical procedures, such as Laser-Assisted in situ Keratomileusis (LASIK) surgery. For instance, a complication known as post-LASIK ectasia may occur due to the thinning and weakening of the cornea caused by LASIK surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

Cross-linking treatments may also be employed to induce refractive changes in the cornea to correct disorders such as myopia, hyperopia, myopia, hyperopia, astigmatism, irregular astigmatism, presbyopia, etc.

SUMMARY

To treat keratoconus or to achieve refractive correction, for instance, an effective cross-linking procedure applies photoactivating light as precisely as possible to specified areas of a cornea treated with a cross-linking agent. Application of the photoactivating light outside the specified areas might generate undesired structural changes in the cornea and negatively affect treatment results. Precise application of the photoactivating light, however, may be difficult to achieve due to eye movement that may occur during the procedure. Such eye movement, for instance, might include translation along a plane (transverse to corneal depth), changes in gaze angle, and/or bulk head motion. Because a cross-linking procedure might require exposing the cornea to the photoactivating light for at least a minute, e.g., one to twenty minutes, some eye movement is very likely to occur during the procedure. To address the occurrence of eye movement, systems and methods can employ an active eye tracking system to determine any changes in the position of the cornea and, in response, an illumination system can be adjusted to apply photoactivating light precisely to specified areas of the cornea.

According to an example embodiment, a system for applying a cross-linking treatment to a cornea of an eye includes a light source configured to emit a photoactivating light. The system includes a spatial light modulator configured to receive the photoactivating light from the light source and provide a pixelated illumination with the photoactivating light. The spatial light modulator defines a maximum area for the pixelated illumination. The system includes a controller configured to cause the spatial light modulator to project a first pixelated illumination onto the cornea to generate cross-linking activity in a treatment area by photoactivating a cross-linking agent applied to the treatment area. The first pixelated illumination has an area that is smaller than the maximum area defined by the spatial light modulator. The controller is further configured to determine movement of the cornea. In response to the movement of the cornea, the controller controls the spatial light modulator to project a second pixelated illumination to the treatment area based on at least one of a translation or transformation of the first pixelated illumination to continue photoactivating the cross-linking agent applied to the treatment area.

In the example embodiment above, using a smaller pixelated illumination can provide a greater range of positional adjustments for the spatial light modulator. Smaller pixelated illumination patterns, however, are composed of fewer pixels. Decreasing the size of pixelated illumination might degrade the minimum resolvable spatial feature that can be projected onto the eye and can produce "pixelation" artifacts. To address such effects, a system for applying a cross-linking treatment to a cornea of an eye includes a light source configured to emit a photoactivating light. The system includes a spatial light modulator configured to receive the photoactivating light from the light source and provide a pixelated illumination with the photoactivating light. The system includes a controller configured to cause the spatial light modulator to project a first pixelated illumination and a second pixelated illumination onto a cornea to generate cross-linking activity in a desired treatment area by photoactivating a cross-linking agent applied to the desired treatment area. The desired treatment area includes at least one portion that is not illuminated by the first pixelated illumination. The second pixelated illumination includes one or more pixels that illuminate the at least one portion of the desired treatment area that is not illuminated by the first pixelated illumination. The spatial light modulator projects the first pixelated illumination and the second pixelated illumination to the cornea according to different temporal parameters. For instance, the first pixelated illumination includes all complete pixels that can be projected within the desired treatment area, and the one or more pixels of the second pixelated illumination include remaining pixels that, in combination with the pixels of the first pixelated illumination, illuminate the entire desired treatment area.

Figure 1:
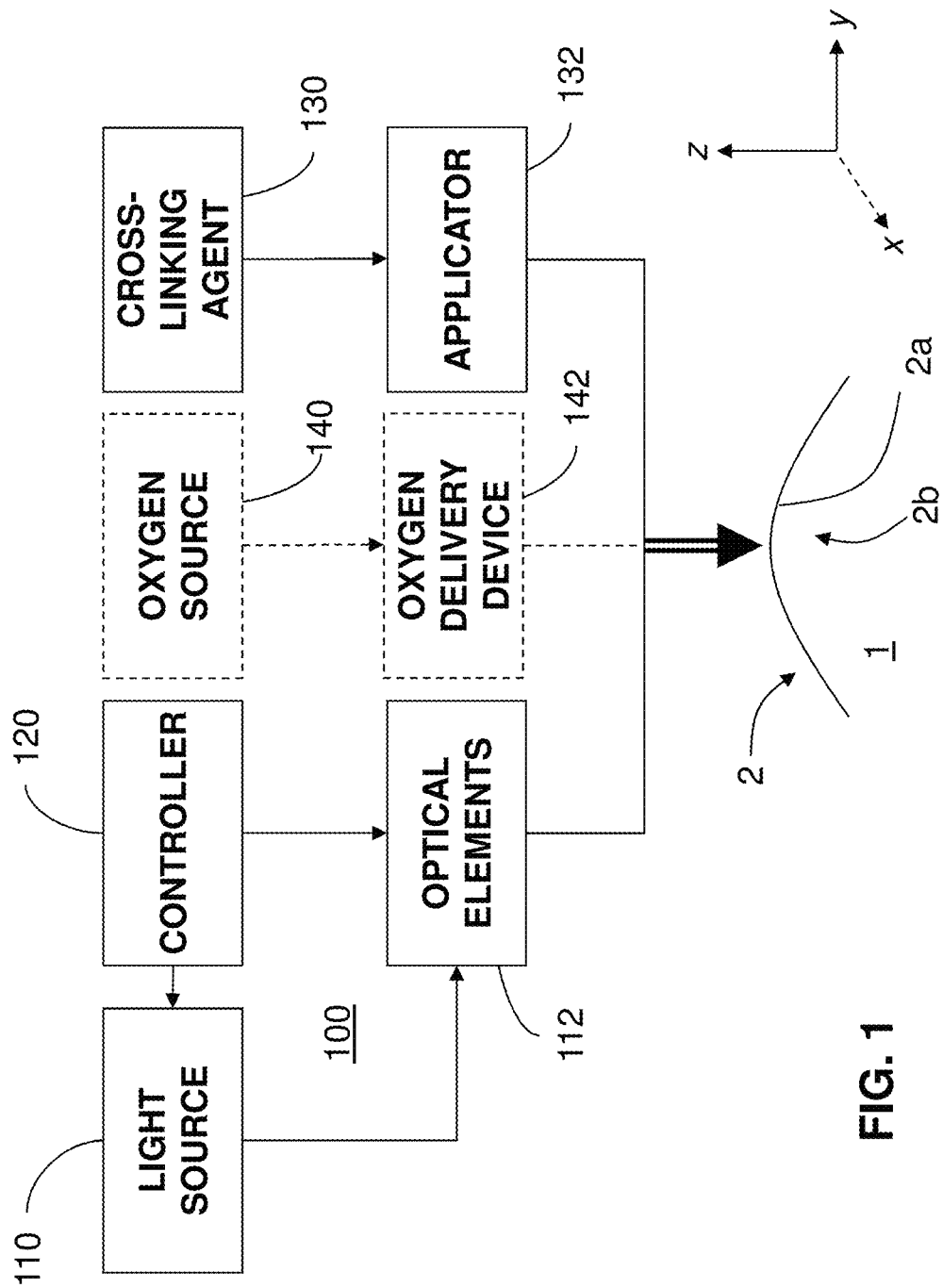
FIG. 1 illustrates an example system that delivers a cross-linking agent and photoactivating light to a cornea of an eye in order to generate cross-linking of corneal collagen, according to aspects of the present disclosure.

While the present disclosure is susceptible to various modifications and alternative forms, a specific embodiment thereof has been shown by way of example in the drawings and will herein be described in detail. It should be understood, however, that it is not intended to limit the present disclosure to the particular forms disclosed, but on the contrary, the intention is to cover all modifications, equivalents, and alternatives falling within the spirit of the present disclosure.

DESCRIPTION

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the photosensitizer 130 as drops to the cornea 2. Example systems and methods for applying the cross-linking agent is described in U.S. Patent Application Publication No. 2017/0296383, filed Apr. 13, 2017 and titled "Systems and Methods for Delivering Drugs to an Eye," the contents of which are incorporated entirely herein by reference.

The cross-linking agent 130 may be provided in a formulation that allows the cross-linking agent 130 to pass through the corneal epithelium 2a and to underlying regions in the corneal stroma 2b. Alternatively, the corneal epithelium 2a may be removed or otherwise incised to allow the cross-linking agent 130 to be applied more directly to the underlying tissue.

The treatment system 100 includes an illumination system with a light source 110 and optical elements 112 for directing light to the cornea 2. The light causes photoactivation of the cross-linking agent 130 to generate cross-linking activity in the cornea 2. For example, the cross-linking agent may include riboflavin and the photoactivating light may include ultraviolet A (UVA) (e.g., approximately 365 nm) light. Alternatively, the photoactivating light may include another wavelength, such as a visible wavelength (e.g., approximately 452 nm). As described further below, corneal cross-linking improves corneal strength by creating chemical bonds within the corneal tissue according to a system of photochemical kinetic reactions. For instance, riboflavin and the photoactivating light may be applied to stabilize and/or strengthen corneal tissue to address diseases such as keratoconus or post-LASIK ectasia.

The treatment system 100 includes one or more controllers 120 that control aspects of the system 100, including the light source 110 and/or the optical elements 112. In an implementation, the cornea 2 can be more broadly treated with the cross-linking agent 130 (e.g., with an eye dropper, syringe, etc.), and the photoactivating light from the light source 110 can be selectively directed to regions of the treated cornea 2 according to a particular pattern.

The optical elements 112 may include one or more mirrors or lenses for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for photoactivating the cross-linking agent 130. In addition, the optical elements 112 may include one or more beam splitters for dividing a beam of light emitted by the light source 110, and may include one or more heat sinks for absorbing light emitted by the light source 110. The optical elements 112 may also accurately and precisely focus the photo-activating light to particular focal planes within the cornea 2, e.g., at a particular depths in the underlying region 2b where cross-linking activity is desired.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of: wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking. In an example implementation, the time can be reduced from minutes to seconds. While some configurations may apply the photoactivating light at an irradiance of 5 mW/cm$^2$, larger irradiance of the photoactivating light, e.g., multiples of 5 mW/cm$^2$, can be applied to reduce the time required to achieve the desired cross-linking. The total dose of energy absorbed in the cornea 2 can be described as an effective dose, which is an amount of energy absorbed through an area of the corneal epithelium 2a. For example the effective dose for a region of the corneal surface 2A can be, for example, 5 J/cm$^2$, or as high as 20 J/cm$^2$ or 30 J/cm$^2$. The effective dose described can be delivered from a single application of energy, or from repeated applications of energy.

The optical elements 112 of the treatment system 100 may include a microelectromechanical system (MEMS) device, e.g., a digital micro-mirror device (DMD), to modulate the application of photoactivating light spatially and temporally. Using DMD technology, the photoactivating light from the light source 110 is projected in a precise spatial pattern that is created by microscopically small mirrors laid out in an array on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for pre-treatment planning and/or real-time monitoring and modulation of corneal cross-linking during treatment. Aspects of a dosimetry system are described in further detail below. Additionally, pre-clinical patient information may be combined with finite element biomechanical computer modeling to create patient specific pre-treatment plans.

To control aspects of the delivery of the photoactivating light, embodiments may also employ aspects of multiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than light of shorter wavelengths. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, the irradiance and the dose of photoactivating light affect the amount and the rate of cross-linking.

When the cross-linking agent 130 is riboflavin in particular, the UVA light may be applied continuously (CW) or as pulsed light, and this selection has an effect on the amount, the rate, and the extent of cross-linking. If the UVA light is applied as pulsed light, the duration of the exposure cycle, the dark cycle, and the ratio of the exposure cycle to the dark cycle duration have an effect on the resulting corneal stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 1 mW/cm$^2$ to approximately 1000 mW/cm$^2$ average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or opto-electronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea to allow for various amounts of refractive correction. These refractive corrections, for instance, may involve combinations of myopia, hyperopia, astigmatism, irregular astigmatism, presbyopia and complex corneal refractive surface corrections because of ophthalmic conditions such as keratoconus, pellucid marginal disease, post-LASIK ectasia, and other conditions of corneal biomechanical alteration/degeneration, etc. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference.

The addition of oxygen also affects the amount of corneal stiffening. In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved. Oxygen may be applied during the cross-linking treatments in a number of different ways. One approach involves supersaturating the riboflavin with $O_2$. Thus, when the riboflavin is applied to the eye, a higher concentration of $O_2$ is delivered directly into the cornea with the riboflavin and affects the reactions involving $O_2$ when the riboflavin is exposed to the photoactivating light. According to another approach, a steady state of $O_2$ (at a selected concentration) may be maintained at the surface of the cornea to expose the cornea to a selected amount of $O_2$ and cause $O_2$ to enter the cornea. As shown in FIG. 1, for instance, the treatment system 100 also includes an oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Patent Application Publication No. 2013/0060187, filed Oct. 31, 2012 and titled "Systems and Methods for Corneal Cross-Linking with Pulsed Light," the contents of these applications being incorporated entirely herein by reference. Additionally, an example mask device for delivering concentrations of oxygen as well as photoactivating light in eye treatments is described in U.S. Patent Application Publication No. 2017/0156926, filed Dec. 3, 2016 and titled "Systems and Methods for Treating an Eye with a Mask Device," the contents of which are incorporated entirely herein by reference. For instance, a mask may be placed over the eye(s) to produce a consistent and known oxygen concentration above the surface.

When riboflavin absorbs radiant energy, especially light, it undergoes photo activation. There are two photochemical kinetic pathways for riboflavin photoactivation, Type I and Type II. The reactions involved in both the Type I and Type II mechanisms and other aspects of the photochemical kinetic reactions generating cross-linking activity are described in U.S. Patent Application Publication No. 2016/0310319, filed Apr. 27, 2016 and titled "Systems and Methods for Cross-Linking Treatments of an Eye," the contents of which are incorporated entirely herein by reference.

To treat keratoconus or to achieve refractive correction for instance, an effective cross-linking procedure applies photoactivating light as precisely as possible to specified areas of a cornea treated with a cross-linking agent. Application of the photoactivating light outside the specified areas might generate undesired structural changes in the cornea and negatively affect treatment results. Precise application of the photoactivating light, however, may be difficult to achieve due to eye movement that may occur during the procedure. Such eye movement, for instance, might include translation along the x-y plane as shown in FIG. 1, changes in gaze angle, and/or bulk head motion. (In FIG. 1, the depth of the cornea 2 is measured along a z-axis and patterns of photoactivating light may be projected on transverse x-y planes.) Because a cross-linking procedure might require exposing the cornea to the photoactivating light for at least one minute, e.g., one to twenty minutes, some eye movement is very likely to occur during the procedure.

Figure 2A:
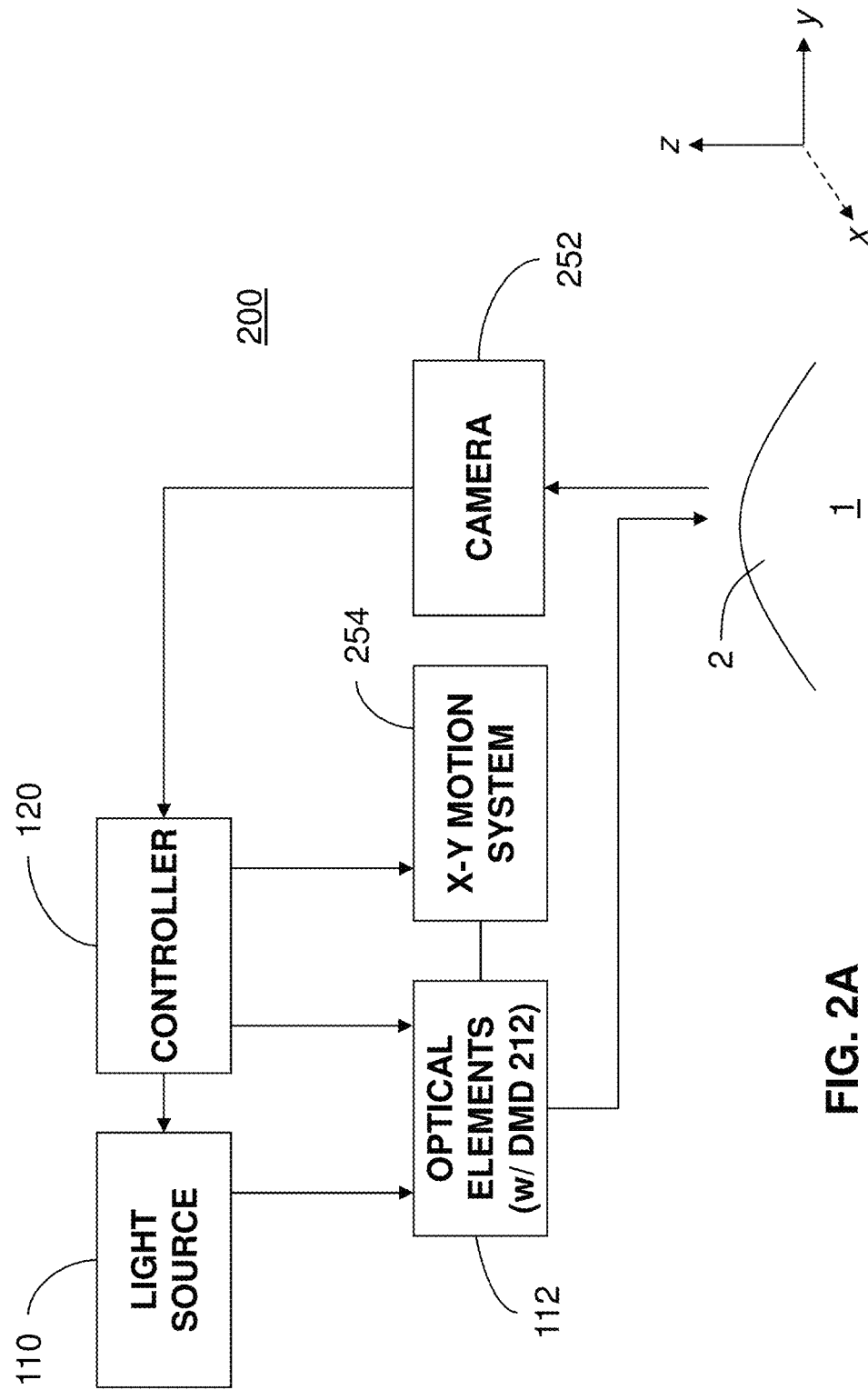
FIG. 2A illustrates an example treatment system with an active eye tracking system, according to aspects of the present disclosure.

To address the occurrence of eye movement, embodiments can employ an active eye tracking system to determine any changes in the position of the cornea and, in response, the illumination system can be adjusted to apply photoactivating light precisely to specified areas of the cornea. FIG. 2A illustrates an example treatment system 200 with an active eye tracking system. The treatment system 200 includes an illumination system for directing photoactivating light to the cornea 2 of the eye 1. The illumination system includes the light source 110 and the optical elements 112 as described above. The light source 110, for instance, may include one or more LED's that emit UV light to photoactivate riboflavin that has been applied to the cornea 2. The optical elements 112, including a DMD 212, project the photoactivating light in a precise spatial pattern onto the cornea 2 along an x-y plane. Additionally, the treatment system 200 includes one or more controllers 120 to control aspects of the treatment system 200.

For the active eye tracking system, the treatment system 200 includes a camera (image capture device) 252 that dynamically captures images of the eye 1 during a procedure. The one or more controllers 120 can process the images to detect a position of a fiducial point, such as the pupil, for the eye 1 relative to the treatment system 200. Using the position of the fiducial point as a reference, the one or more controllers 120 can determine the location of the specified areas of the cornea 2. Thus, the one or more controllers 120 can adjust the treatment system 200 to deliver the photoactivating light to the location of the specified areas. In some cases, the camera 252 and the software (e.g., computer-readable instructions stored on a non-transitory medium) for processing the images and adjusting the treatment system 200 may collectively be known as a vision system.

Figure 2B:
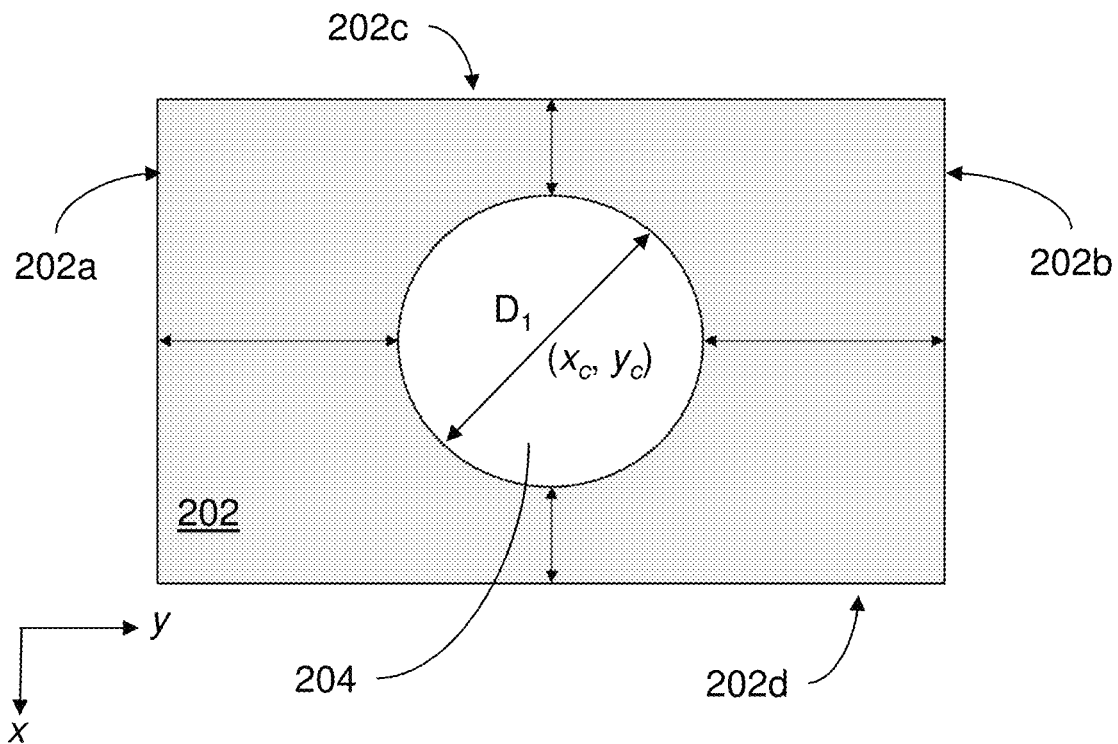
FIG. 2B illustrates an illumination pattern for the example treatment system of FIG. 2A.

Referring to FIG. 2B, the entire mirror array of the DMD 212 defines a maximum area 202 for delivering photoactivating light. The maximum area 202 includes boundaries 202a-d. Any part of the array of the DMD 212 can be activated to deliver photoactivating light from any portion of the maximum area 202. For instance, as shown in FIG. 2B, a part of the array of the DMD 212 can be activated to produce an illumination pattern 204 that is substantially circular and centered at a position $(x_c, y_c)$ with a diameter $D_1$. The diameter $D_1$ of the illumination pattern 204 may be slightly smaller than the distance along the y-axis between the opposing boundaries 202a, b and the distance along the x-axis between the opposing boundaries 202c, d. As such, there may be space between the illumination pattern 204 and the boundaries 202a-d. This space allows the center of the illumination pattern 204 to be translated a small distance within the area 202 while maintaining the same shape with the diameter $D_1$. For instance, another part of the array of the DMD 212 can be activated to produce the illumination pattern 204 centered at a different position $(x_c+\delta_{x1}, y_c+\delta_{y1})$, where $\delta_{x1}$ represents possible translation along the x-axis and $\delta_{y1}$ represents possible translation along the y-axis. The translation of the illumination pattern 204 within the area 202 changes the position of corresponding photoactivating light as delivered to the cornea 2. Thus, in response to eye movement detected via the camera 252, the one or more controllers 120 can control the DMD 212 to adjust the delivery of the photoactivating light so that it reaches specified areas of the cornea 2 to achieve desired results.

The adjustments that the one or more controllers 120 can make with the DMD 212, however, are limited by the small amount of space between the illumination pattern 204 and the boundaries 202a-d. With the DMD 212 alone, the one or more controllers 120 might be unable to make sufficiently large adjustments to the position of the illumination pattern 204 within the area 202 to respond to larger eye movements. In other words, the illumination pattern 204 might reach one of the boundaries 202a-d before the illumination pattern 204 can be moved a desired distance. To make larger adjustments that cannot be made with the DMD 212, the treatment system 200 includes an electromechanical X-Y motion system 254 coupled to one or more of the optical elements 112. The one or more controllers 120 can control the X-Y motion system 254 to move one or more of the optical elements 112 into better mechanical alignment with the cornea 2 in response to larger eye movement. For instance, the X-Y motion system 254 may include electromechanical stages that can be operated to move one or more of the optical elements 112 and the corresponding photoactivating light along the x-axis and/or the y-axis. Thus, the treatment system 200 employs the DMD 212 for smaller adjustments and the X-Y motion system 254 for larger adjustments in response to varying amounts of eye movement.

Figure 3B:
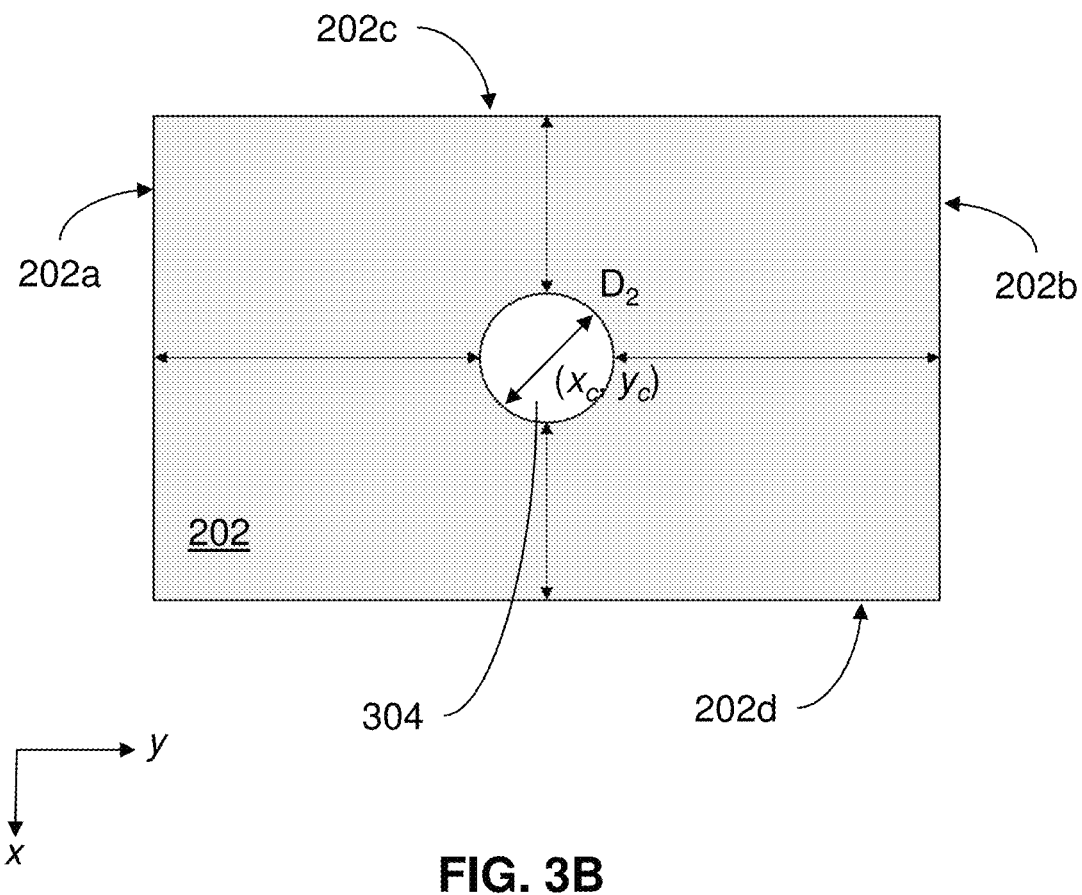
FIG. 3B illustrates an illumination pattern for the example treatment system of FIG. 3A.
Figure 3A:
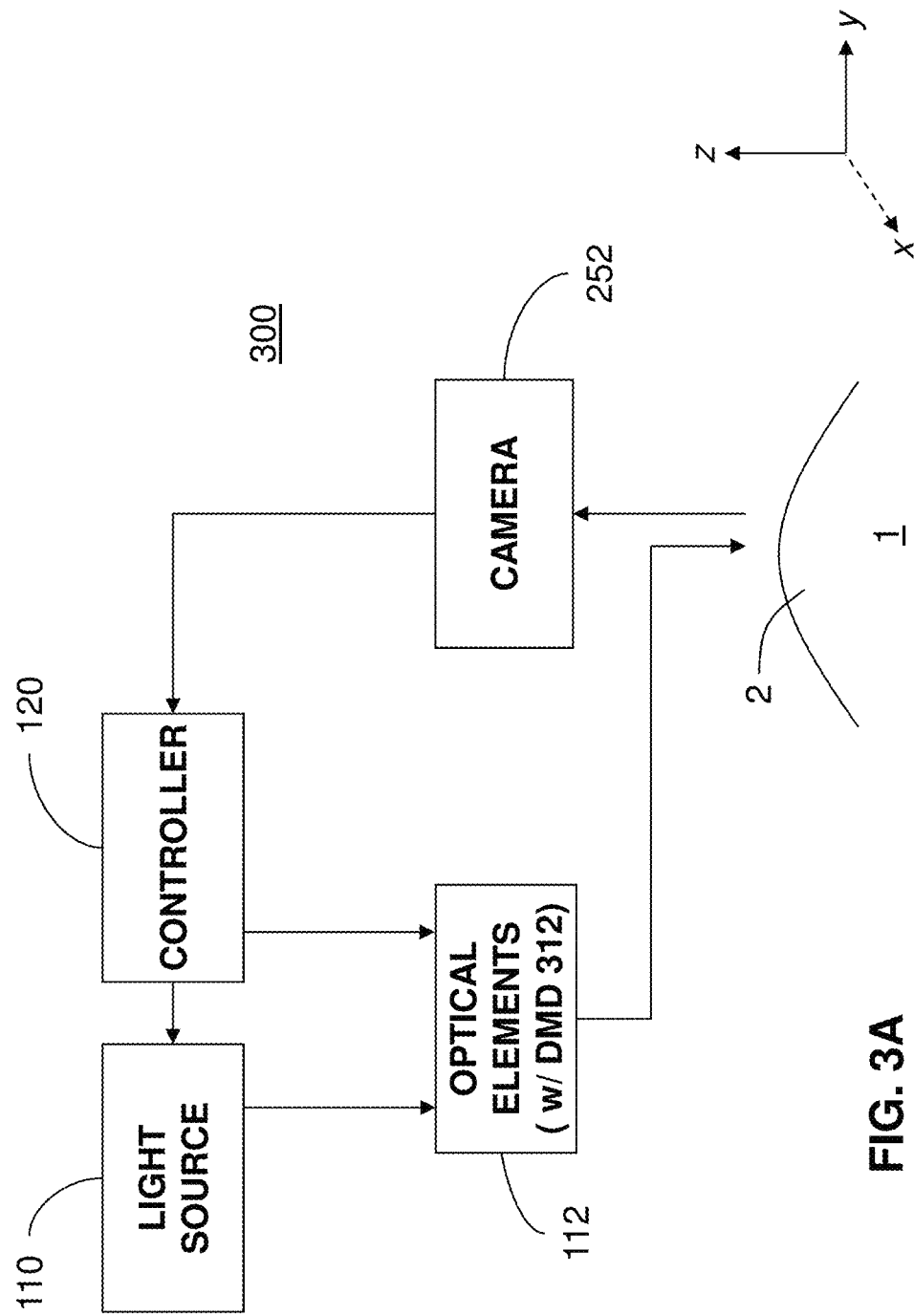
FIG. 3A illustrates an example treatment system with an alternative active eye tracking system, according to aspects of the present disclosure.

FIG. 3A illustrates an example treatment system 300 with an alternative active eye tracking system. In contrast to the treatment system 200 shown in FIG. 2A, the treatment system 300 does not employ the X-Y motion system 254. Rather, the treatment system 300 uses a DMD 312 to make substantially all desired adjustments digitally. Similar to the DMD 212 above, the entire mirror array in the DMD 312 defines the same maximum area 202 for delivering photoactivating light as shown in FIG. 3B. The maximum area 202 includes the same boundaries 202a-d. Any part of the array of the DMD 312 can be activated to deliver light from any portion of this maximum area 202. To eliminate the need for the X-Y motion system 254 employed for the illumination pattern 204 shown in FIG. 2A, the DMD 312 delivers an illumination pattern 304 that is significantly smaller than the illumination pattern 204.

A comparison of FIGS. 2B, 3B demonstrates the difference between the respective illumination patterns 204, 304 within the same maximum area 202. The smaller area illumination pattern 304 is generated by activating even less of the DMD array. The illumination pattern 304 is substantially circular and centered at a position ($x_c$, $y_c$) but has a diameter $D_2$ that is smaller than the diameter $D_1$ of the illumination pattern 204. As such, there is more space between the illumination pattern 304 and the boundaries 202a-d than between the illumination pattern 204 and the boundaries 202a-d. This greater space allows the center of the illumination pattern 304 to be translated within the area 202 along the x-axis and/or y-axis to a greater degree than the center of the illumination pattern 204. In other words, another part of the array of the DMD 312 can be activated to produce the illumination pattern 304 centered at a different position ($x_c+\delta_{x2}$, $y_c-\delta_{y2}$) where $\delta_{x2}$ is greater than $\delta_{x1}$, $\delta_{y2}$ is greater than $\delta_{y1}$, and $\delta_{x1}$ and $\delta_{y1}$ represent possible translation along respective axes with the treatment system 200.

The translation of the illumination pattern 304 within the area 202 changes the position of corresponding photoactivating light as applied to the cornea 2. Greater possible translation of the illumination pattern 304 with the DMD 312 allows greater range of adjustments for the delivery of the photoactivating light along the x-axis and/or y-axis. Thus, in response to eye movement detected via the camera 252, the one or more controllers 120 can employ the DMD 312 to make substantially all desired adjustments so that the photoactivating light reaches specified areas of the cornea 2 to achieve desired results.

The treatment system 200 relies on the electromechanical X-Y motion system 254, which might employ slower motors. In contrast, the DMD 312 can respond digitally to instructions at rates of approximately 60 Hz, so the treatment system 300 can make positional adjustments to the delivery of photoactivating light more quickly.

Figure 4B:
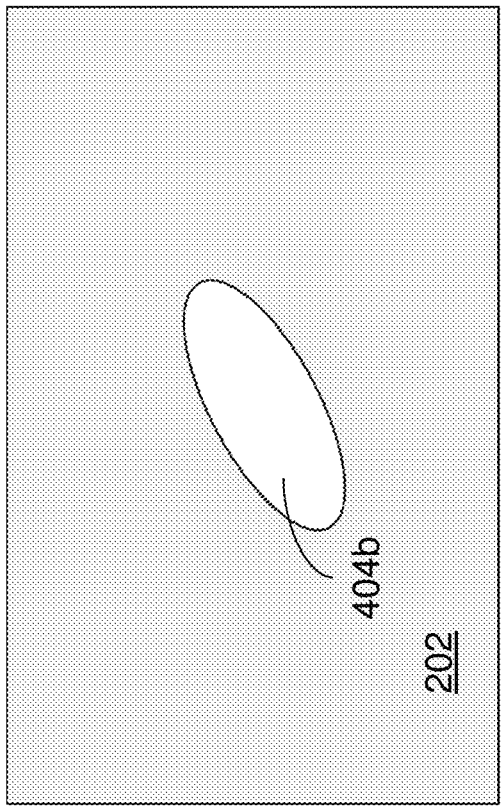
FIG. 4B illustrates another example illumination pattern based on a transformation of the illumination pattern of FIG. 4A in response to a rotational change in a subject eye.
Figure 4A:
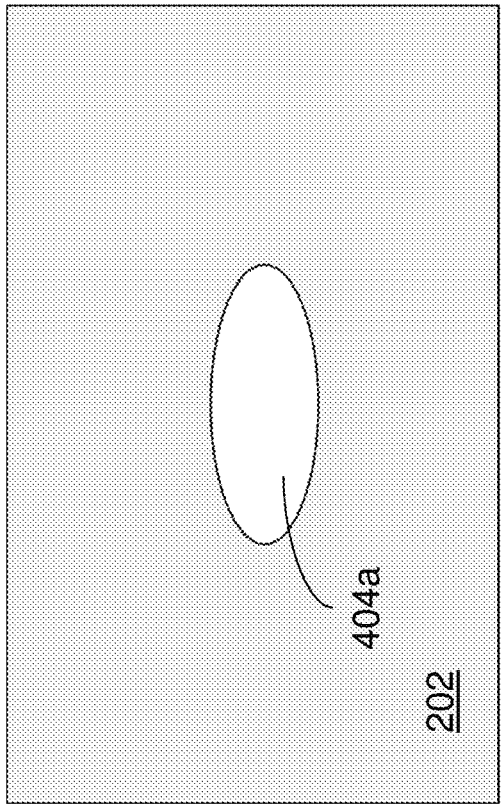
FIG. 4A illustrates an example illumination pattern for the example treatment system of FIG. 3A.

By using the DMD 312, the treatment system 300 can also make other positional corrections that are not possible with the X-Y motion system 254. For instance, the treatment system 300 can respond more effectively to rotational changes in the position of the eye by applying a corresponding rotational transformation to the illumination pattern applied to the eye via the DMD 312. FIG. 4A illustrates an initial illumination pattern 404a generated by activating a portion of the array of the DMD 312. The illumination pattern 404a has an initial rotational state. When the treatment system 300 detects a rotational change in the position of the eye via the camera 252, another portion of the array of the DMD 312 can be activated to generate an illumination pattern 404b shown in FIG. 4B. The illumination pattern 404b provides a geometric transformation of the initial illumination pattern 404a, with a different rotational state that responds to the rotational change in the position of the eye.

Figure 5A:
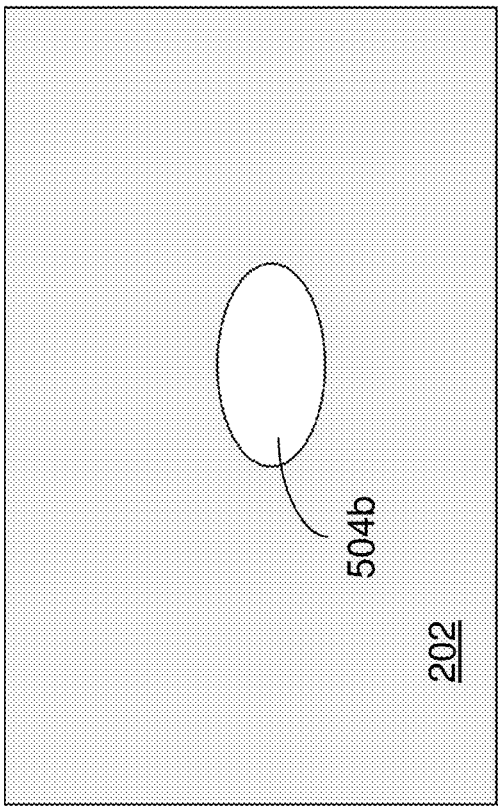
FIG. 5A illustrates an example illumination pattern for the example treatment system of FIG. 3A.
Figure 5B:
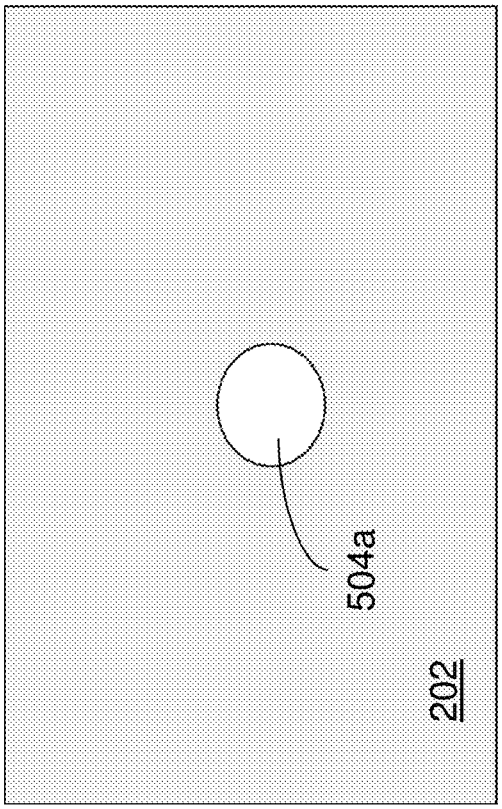
FIG. 5B illustrates another example illumination pattern based on a transformation of the illumination pattern of FIG. 5A in response to a geometric distortion produced by a change in eye gaze angle and/or head movement by a subject.

Additionally, the treatment system 300 can respond more effectively to geometric distortions caused by changes in eye gaze angle and/or head position. For instance, FIG. 5A illustrates an initial illumination pattern 504a generated by activating a portion of the array of the DMD 312. As shown, the illumination pattern 504a is substantially circular. Preferably, the photoactivating light from the treatment system 300 is projected as predicted onto a desired plane (e.g., x-y plane) in the cornea 2 with a corresponding substantially circular shape. A change in eye gaze angle and/or head position, however, may change the angle of the desired plane in the cornea 2 and geometrically distort the projection of the photoactivating light into a shape that is different from the initial illumination pattern 504a. For instance, the change in eye gaze angle and/or head position may cause the illumination pattern 504a to be elongated, so that an elliptical shape is be projected onto the desired plane. When the treatment system 300 detects a change in eye gaze angle and/or head position via the camera 252, another portion of the array of the DMD 312 can be activated to generate an illumination pattern 504b as shown in FIG. 5B. The illumination pattern 504b provides a geometric transformation of the initial illumination pattern 504a, with a different shape that can compensate for the geometric distortion caused by the change in eye gaze angle and/or head position. When the illumination pattern 504b is projected onto the desired plane of the cornea, the projection has precisely the desired shape. In particular, in the example of FIGS. 5A-B, the projection has a substantially circular shape. In other applications, however, the projection may have other desired shapes (e.g., elliptical, etc.)

Figure 6A:
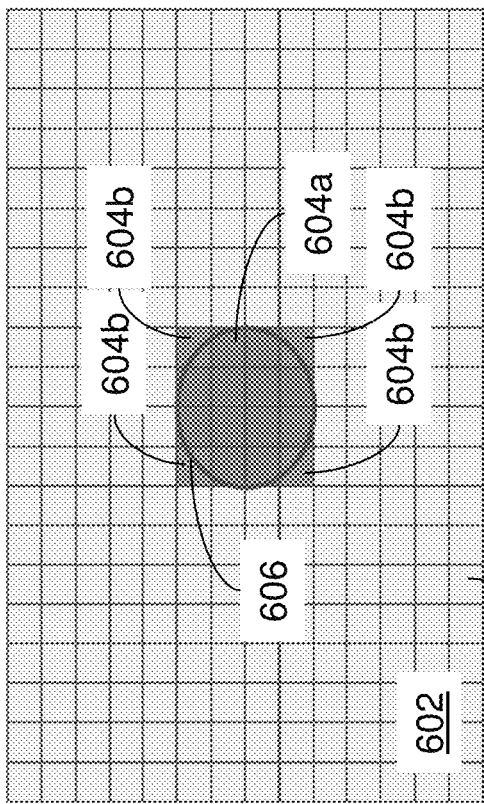
FIG. 6A illustrates an example pixel activation corresponding to a desired illumination pattern for the example treatment system of FIG. 3A.

Using smaller illumination patterns provide a greater range of positional adjustments for the DMD 312. As described above, a DMD provides an illumination pattern that is pixelated according to the array of mirrors. Because illumination patterns from the DMD are composed of a discrete number of pixels, smaller illumination patterns are composed of fewer pixels. As such, decreasing the size of an illumination pattern degrades the minimum resolvable spatial feature that can be projected onto the eye and can produce "pixelation" artifacts. As shown in FIG. 6A, the DMD 312 provides a maximum illumination area 602 defined by a plurality pixels 602a. The treatment system 300 can activate a subset of these pixels to produce a smaller illumination pattern that allows a greater range of positional adjustments. For instance, FIG. 602a illustrates the boundary (outline) of a desired illumination pattern 606. Due to the size of the desired illumination pattern 606, however, only pixels 604a fit substantially within the desired illumination pattern 606. If only the pixels 604a are activated, portions of the desired illumination pattern 606 remain unfilled. If pixels 604b are activated to fill the remaining portions of the desired illumination pattern 606, however, the resulting illumination pattern does not have the desired shape. In either case, the resulting illumination pattern does not have smoothed edges that correspond to the desired illumination pattern 606. In general, the example of FIG. 6A demonstrates, for a given DMD array size, a tradeoff between the range of possible adjustments for active eye tracking with a DMD and resolution for achieving a desired illumination pattern.

Figure 6B:
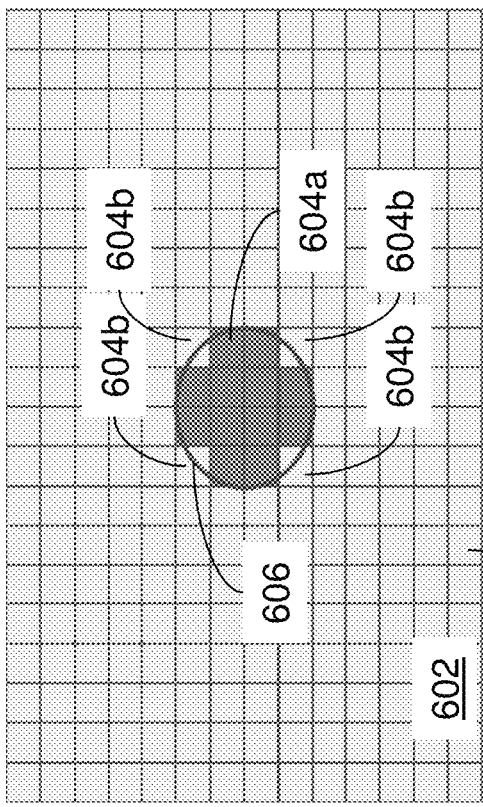
FIG. 6B illustrates an example approach for resolving a pixilation artifact resulting from the pixel activation illustrated by FIG. 6A.

FIG. 6B illustrates an approach for resolving the pixilation artifact illustrated by FIG. 6A and producing an illumination pattern with smoother edges that correspond to the desired illumination pattern 606. In particular, the one or more controllers 120 can operate the DMD 312 to dither the pixels 604b at a rapid rate during the procedure. For instance, the pixels 604b can be alternately activated every second update cycle for the DMD 312. The total dose of photoactivating light delivered by the pixels 604b when dithered during a procedure is less than activating the pixels 604b for the entire duration of the procedure. As such, dithering can be applied to provide a smoother illumination pattern that more closely approximates the desired illumination pattern 606 and the corresponding dose of photoactivating light.

Figure 6C:
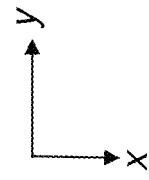
FIG. 6C illustrates another example approach for resolving a pixilation artifact resulting from the pixel activation illustrated by FIG. 6A.
Figure 6C:
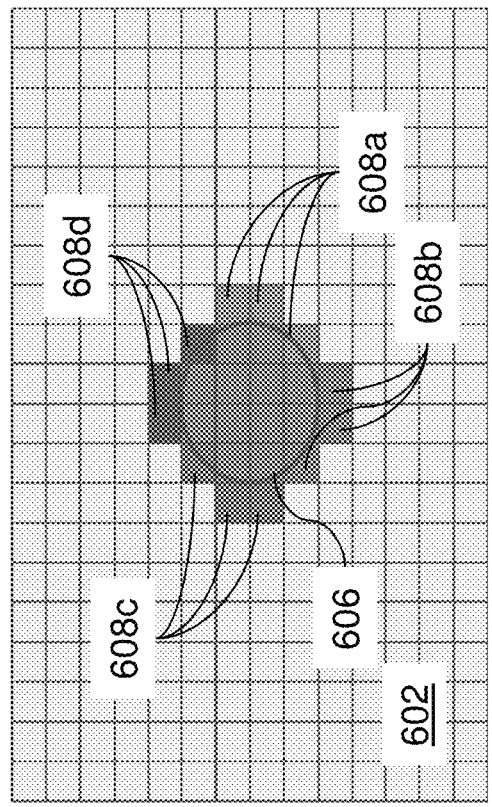

FIG. 6C illustrates another approach for smoothing out the pixilation artifact illustrated by FIG. 6A. In particular, dithering can be applied by alternately shifting a base shape defined by the pixels 604a shown in FIG. 6A by +/−1 pixel along the x-axis or the y-axis at interleaved time points. For instance, at one update cycle, the DMD 312 is operated to translate the base shape by one pixel in the positive-y direction (from the position shown in FIG. 6A) to include boundaries defined partially by the pixels 608a. At the next update cycle, the DMD 312 is operated to translate the base shape by one pixel in the positive-x direction (from the position shown in FIG. 6A) to include boundaries defined partially by the pixels 608b. At the next update cycle, the DMD 312 is operated to translate the base shape by one pixel in the negative-y direction (from the position shown in FIG. 6A) to include boundaries defined partially by the pixels 608c. At the next update cycle, the DMD 312 is operated to translate the base shape by one pixel in the negative-x direction (from the position shown in FIG. 6A) to include boundaries defined partially by the pixels 608d. These series of steps are repeated to provide a smoother illumination pattern that more closely approximates the desired illumination pattern 606 and the corresponding dose of photoactivating light.

The maximum acceptable pixel size for a DMD and optimal parameters for the embodiments above can be determined by biomechanical modeling of the response of the cornea to a cross-linking procedure.

Figure 7A:
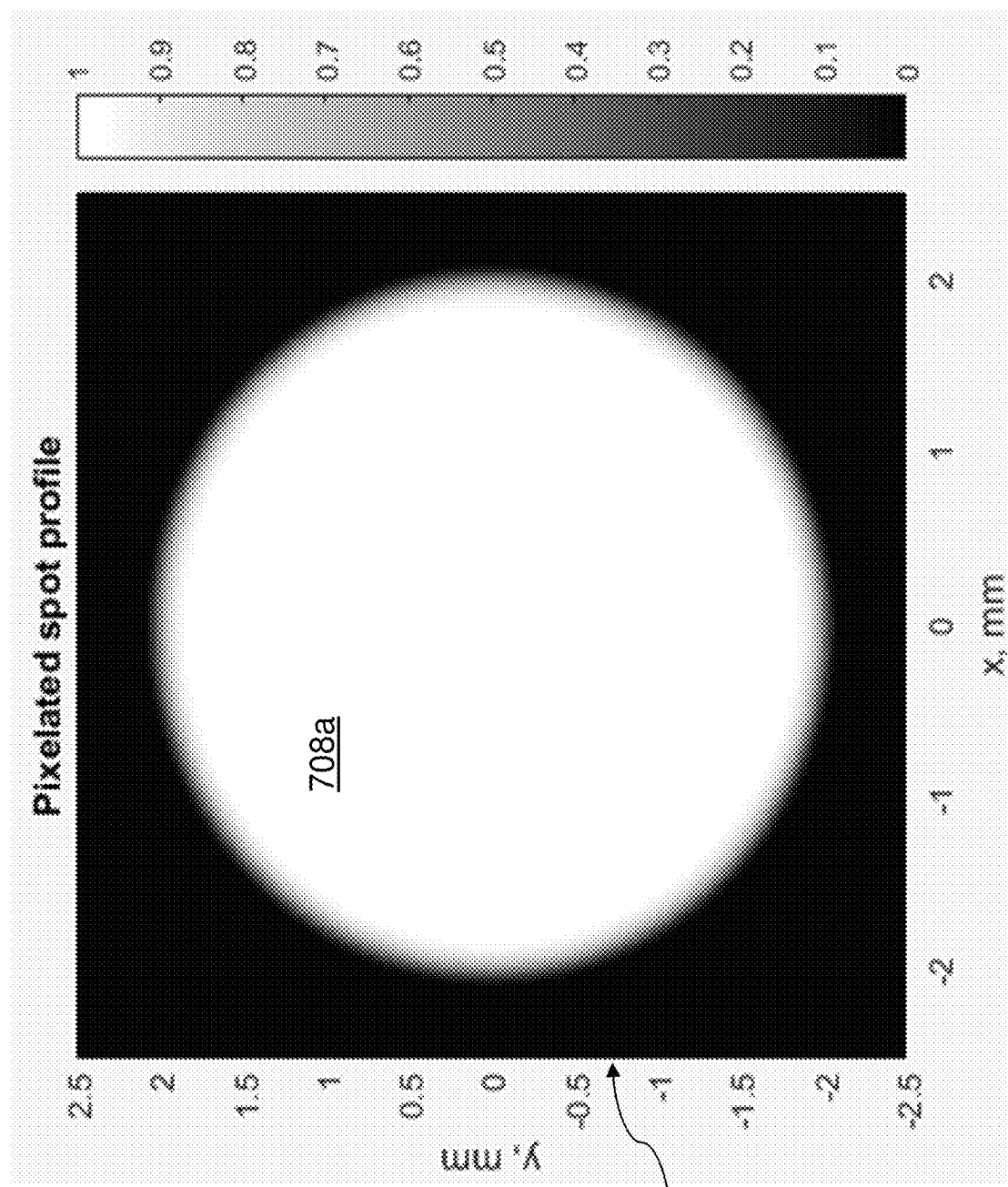
FIG. 7A illustrates a substantially circular UV illumination pattern (diameter=4 mm) defined by pixels that are 25 µm×25 µm in size, according to aspects of the present disclosure.
Figure 7B:
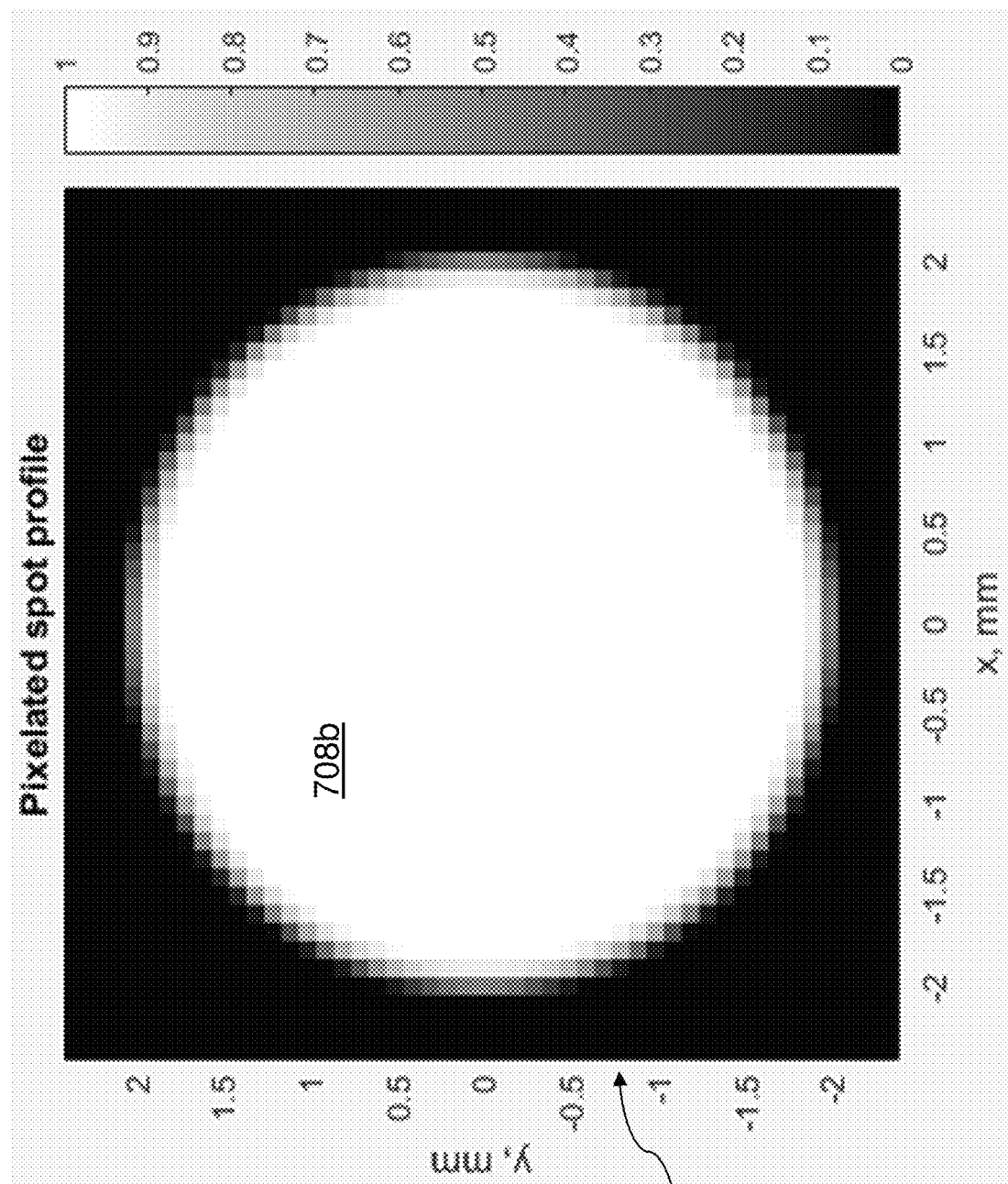
FIG. 7B illustrates a substantially circular UV illumination pattern (diameter=4 mm) defined by pixels that are 100 µm×100 µm in size, according to aspects of the present disclosure.
Figure 7C:
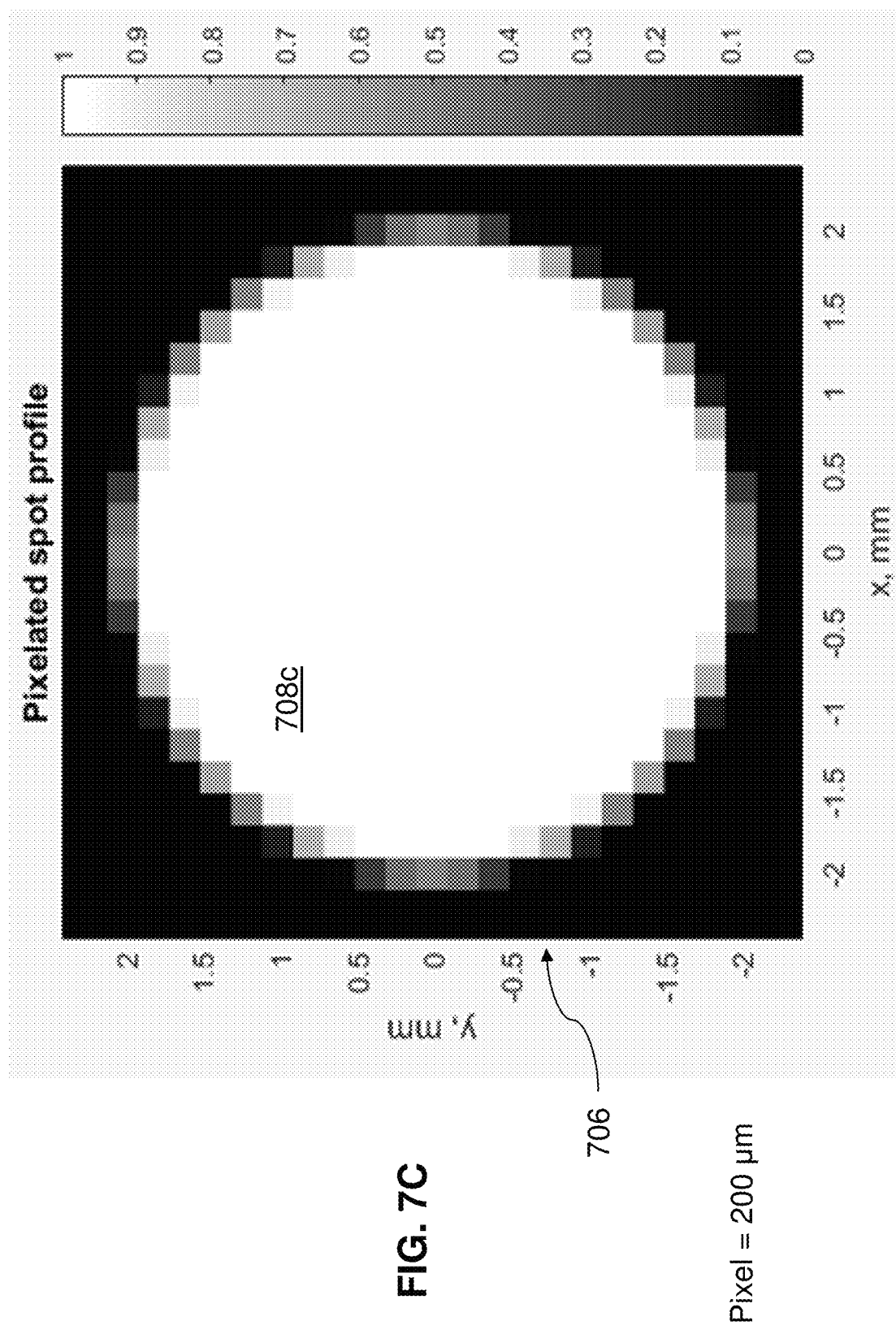
FIG. 7C illustrates a substantially circular UV illumination pattern (diameter=4 mm) defined by pixels that are 200 µm×200 µm in size, according to aspects of the present disclosure.
Figure 7D:
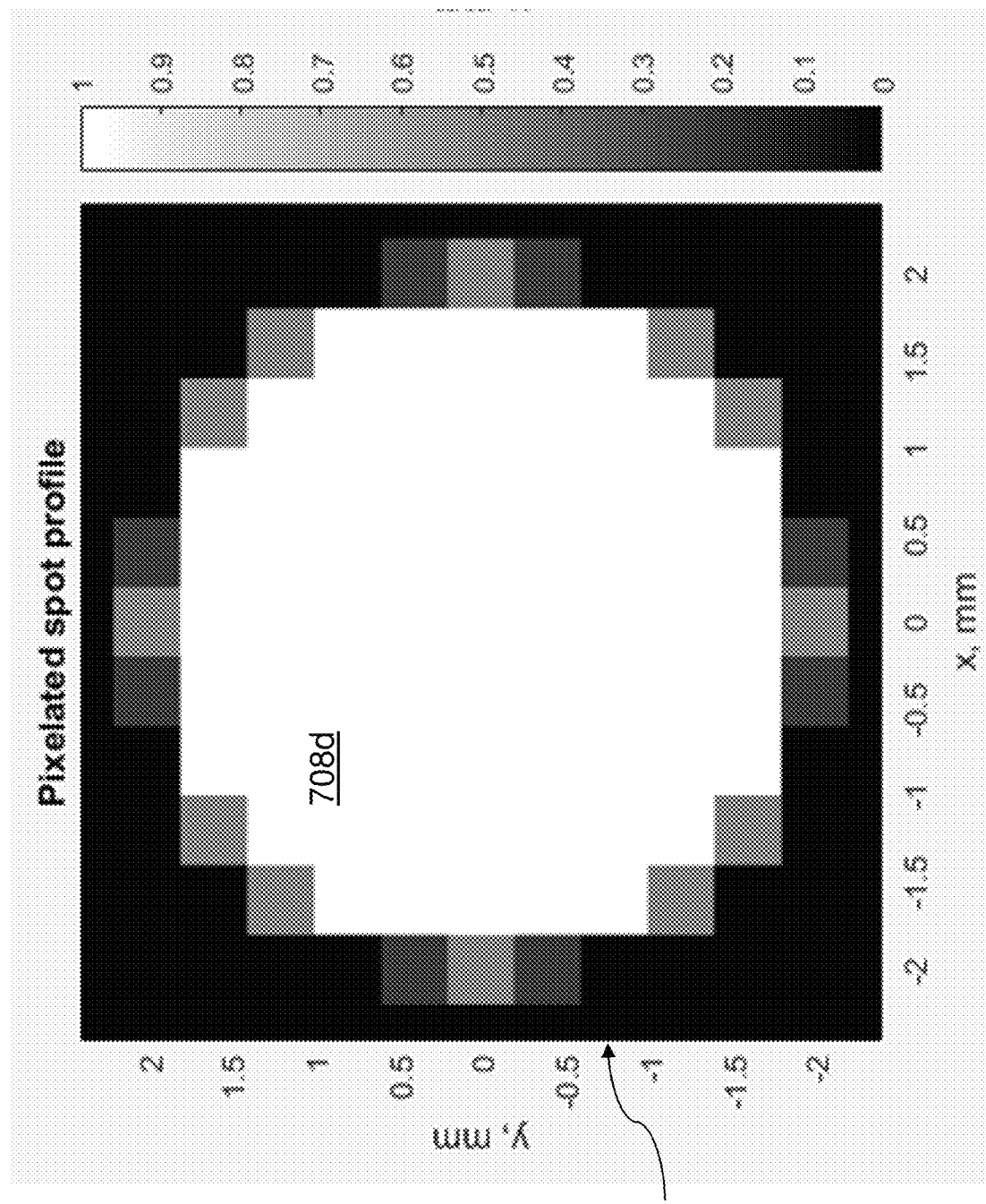
FIG. 7D illustrates a substantially circular UV illumination pattern (diameter=4 mm) defined by pixels that are 400 µm×400 µm in size, according to aspects of the present disclosure.
Figure 7E:
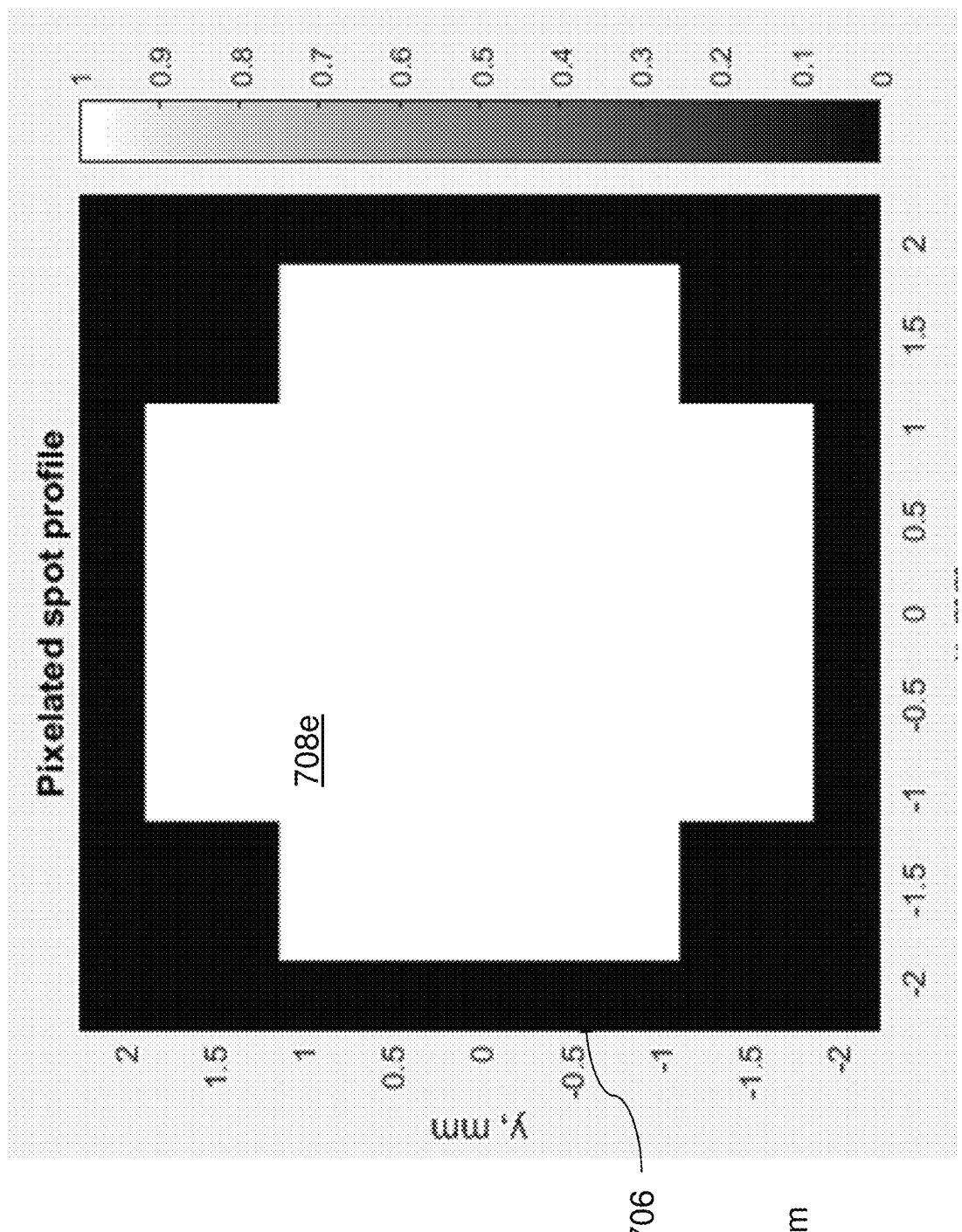
FIG. 7E illustrates a substantially circular UV illumination pattern (diameter=4 mm) defined by pixels that are 750 µm×750 µm in size, according to aspects of the present disclosure.
Figure 7F:
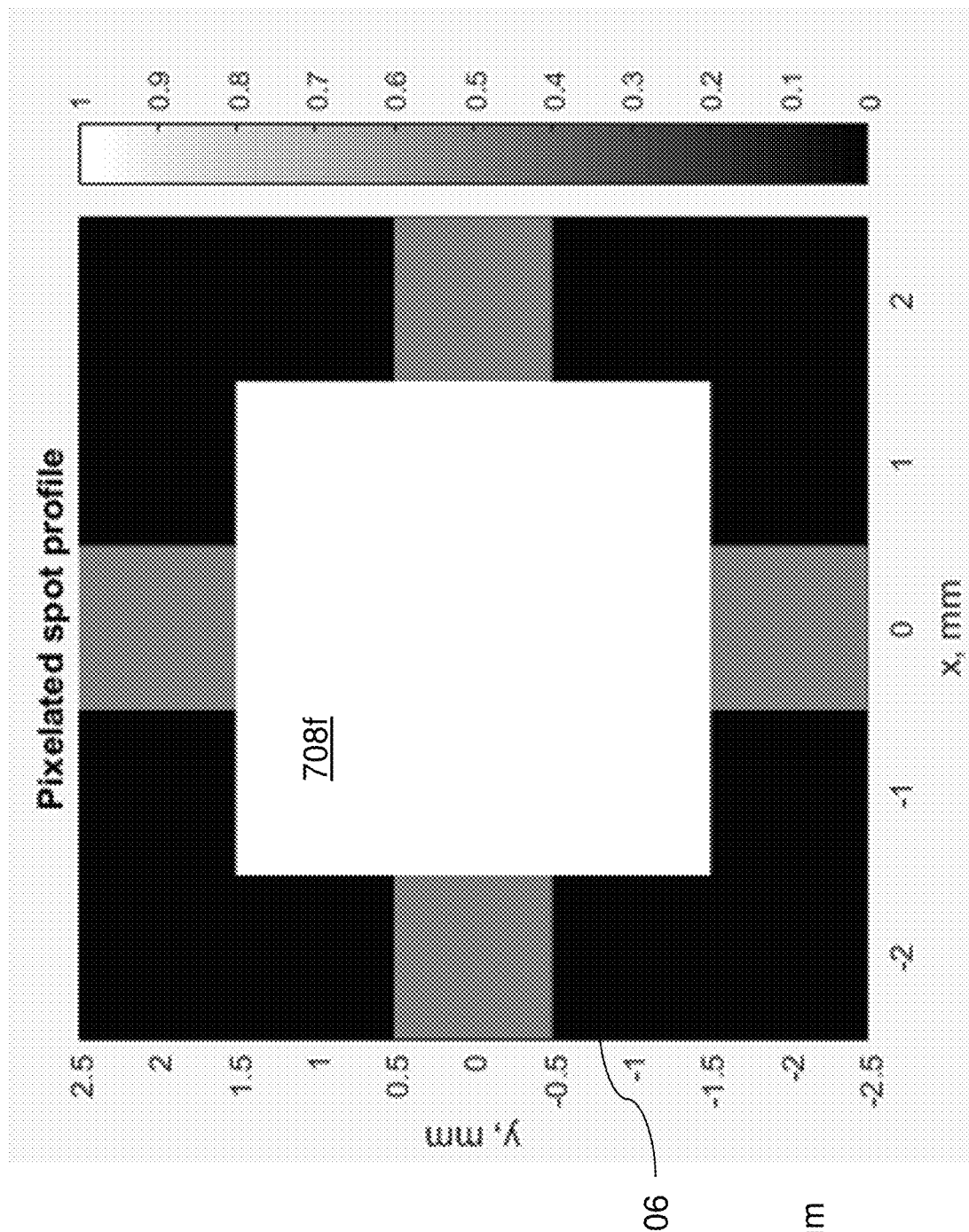
FIG. 7F illustrates a substantially circular UV illumination pattern (diameter=4 mm) defined by pixels that are 1000 µm×1000 µm in size, according to aspects of the present disclosure.

FIGS. 7A-F illustrate the use of increasing pixel size for delivering a substantially circular UV illumination pattern 706 with a diameter of approximately 4 mm. The illumination pattern 706 may be employed, for instance, to generate a corresponding area of cross-linking activity in the cornea to treat myopia. In FIG. 7A, the illumination pattern 706 is defined by pixels 708a, which are 25 µm×25 µm in size. In FIG. 7B, the illumination pattern 706 is defined by pixels 708b, which are 100 µm×100 µm in size. In FIG. 7C, the illumination pattern 706 is defined by pixels 708c, which are 200 µm×200 µm in size. In FIG. 7D, the illumination pattern 706 is defined by pixels 708d, which are 400 µm×400 µm in size. In FIG. 7E, the illumination pattern 706 is defined by pixels 708e, which are 750 µm×750 µm in size. In FIG. 7F, the illumination pattern 706 is defined by pixels 708f, which are 1000 µm×1000 µm in size. The effects of eye motion on the illumination pattern 706 are modeled in FIGS. 7A-F with a 100 µm blurring function along the edge of the illumination pattern 706.

Figure 8A:
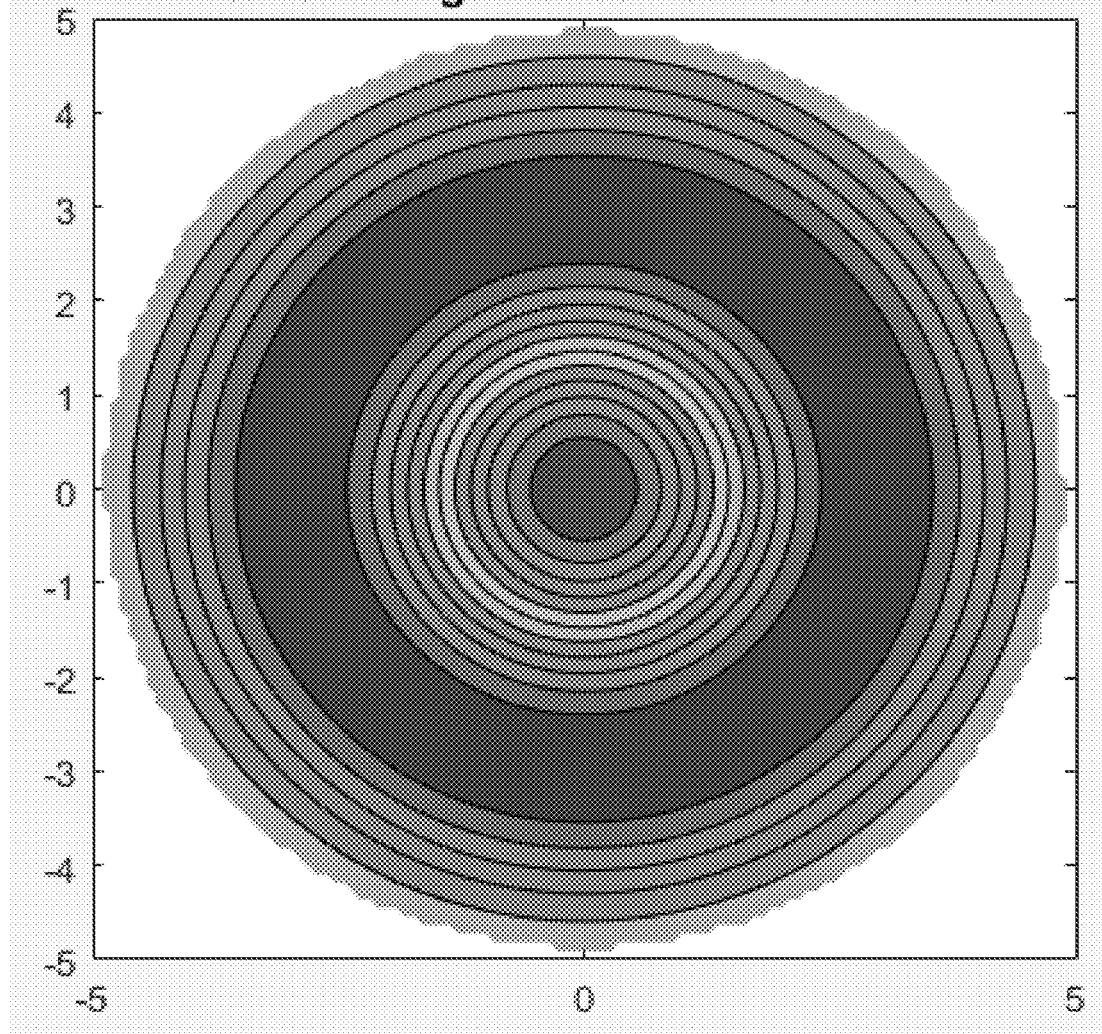
FIG. 8A illustrates modeled changes (from pre-treatment to post-treatment) in tangential curvature of the anterior cornea following cross-linking treatments using the UV illumination pattern defined in FIG. 7A.
Figure 8B:
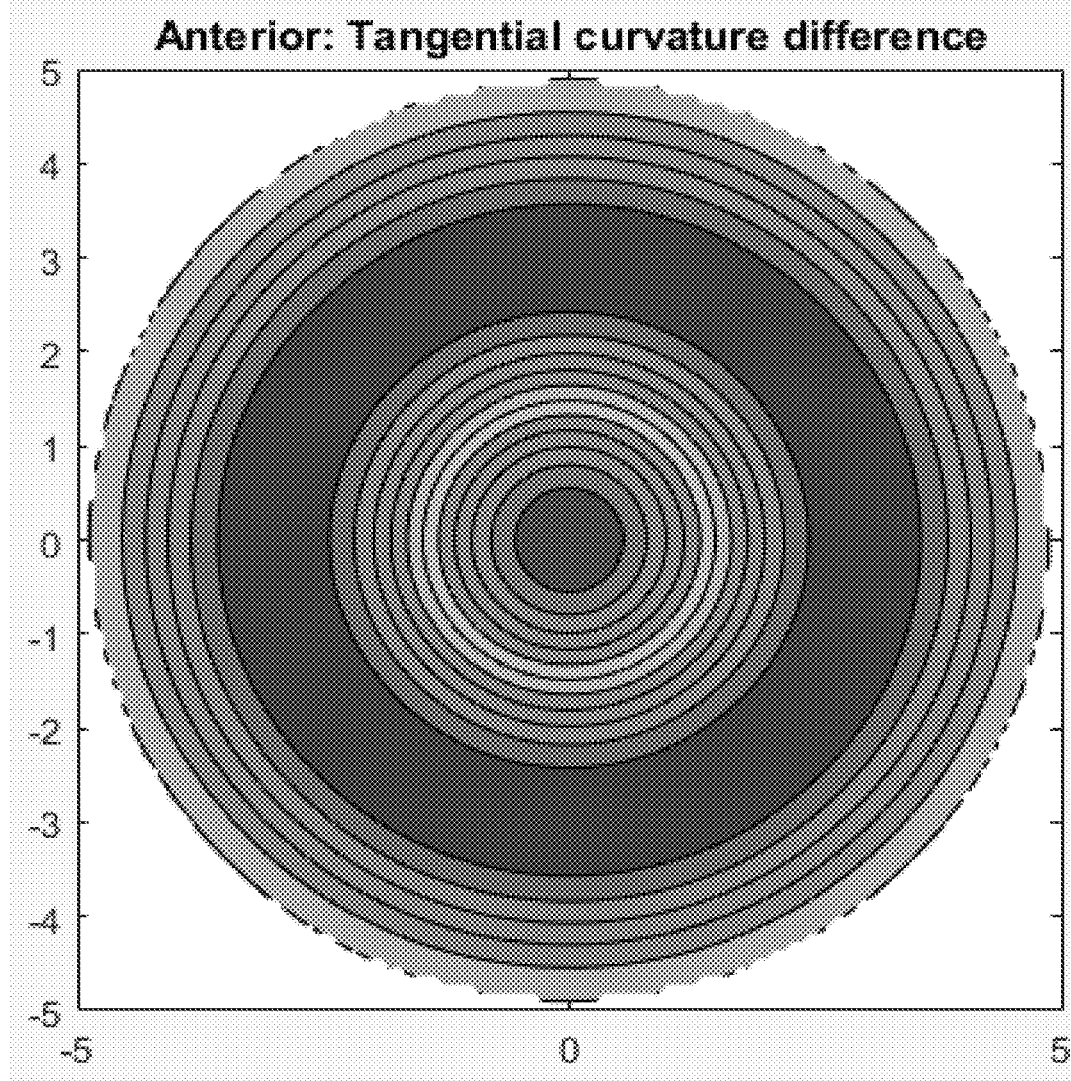
FIG. 8B illustrates modeled changes in tangential curvature of the anterior cornea following cross-linking treatments using the UV illumination pattern defined in FIG. 7B.
Figure 8C:
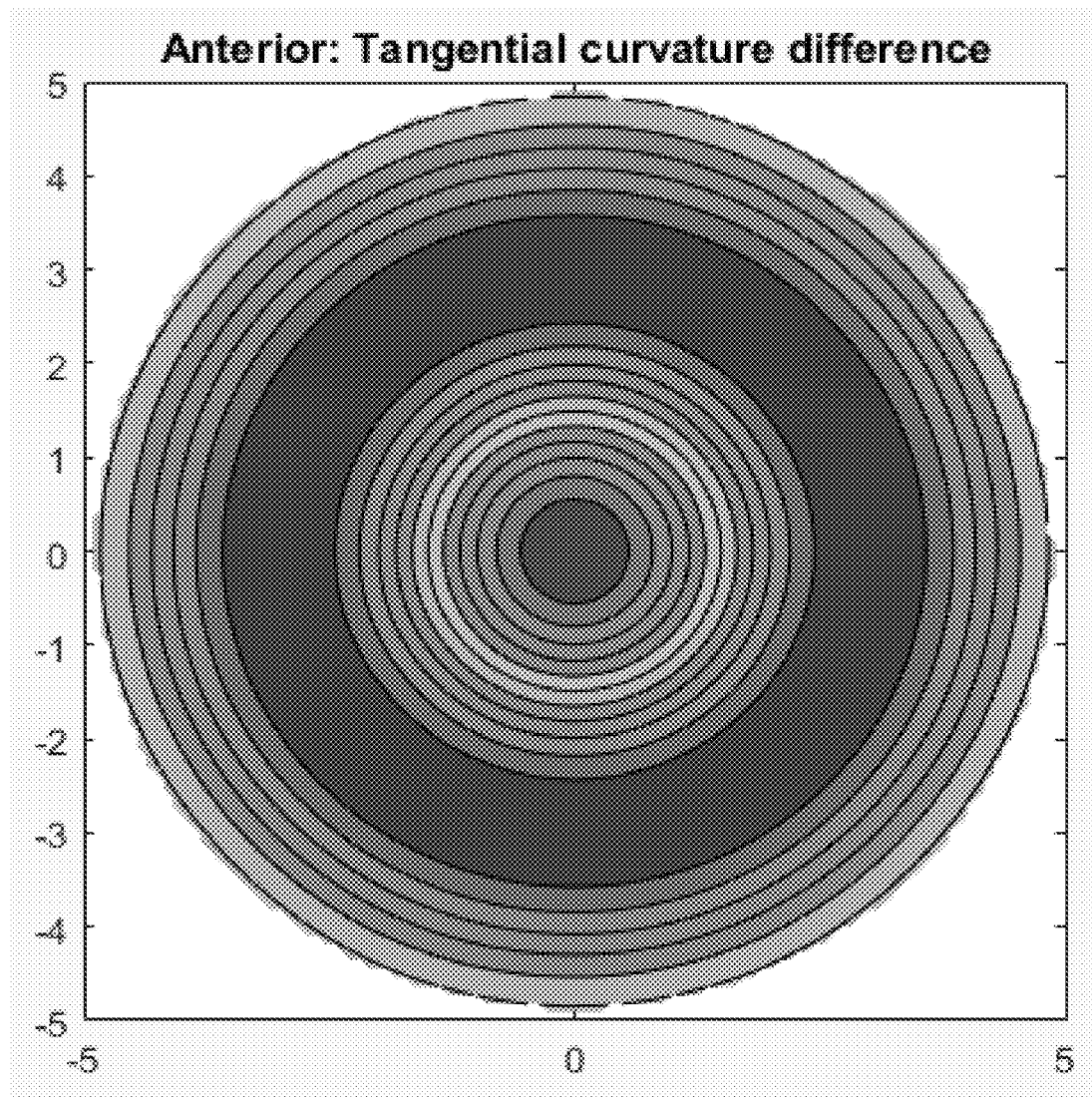
FIG. 8C illustrates modeled changes in tangential curvature of the anterior cornea following cross-linking treatments using the UV illumination pattern defined in FIG. 7C.
Figure 8D:
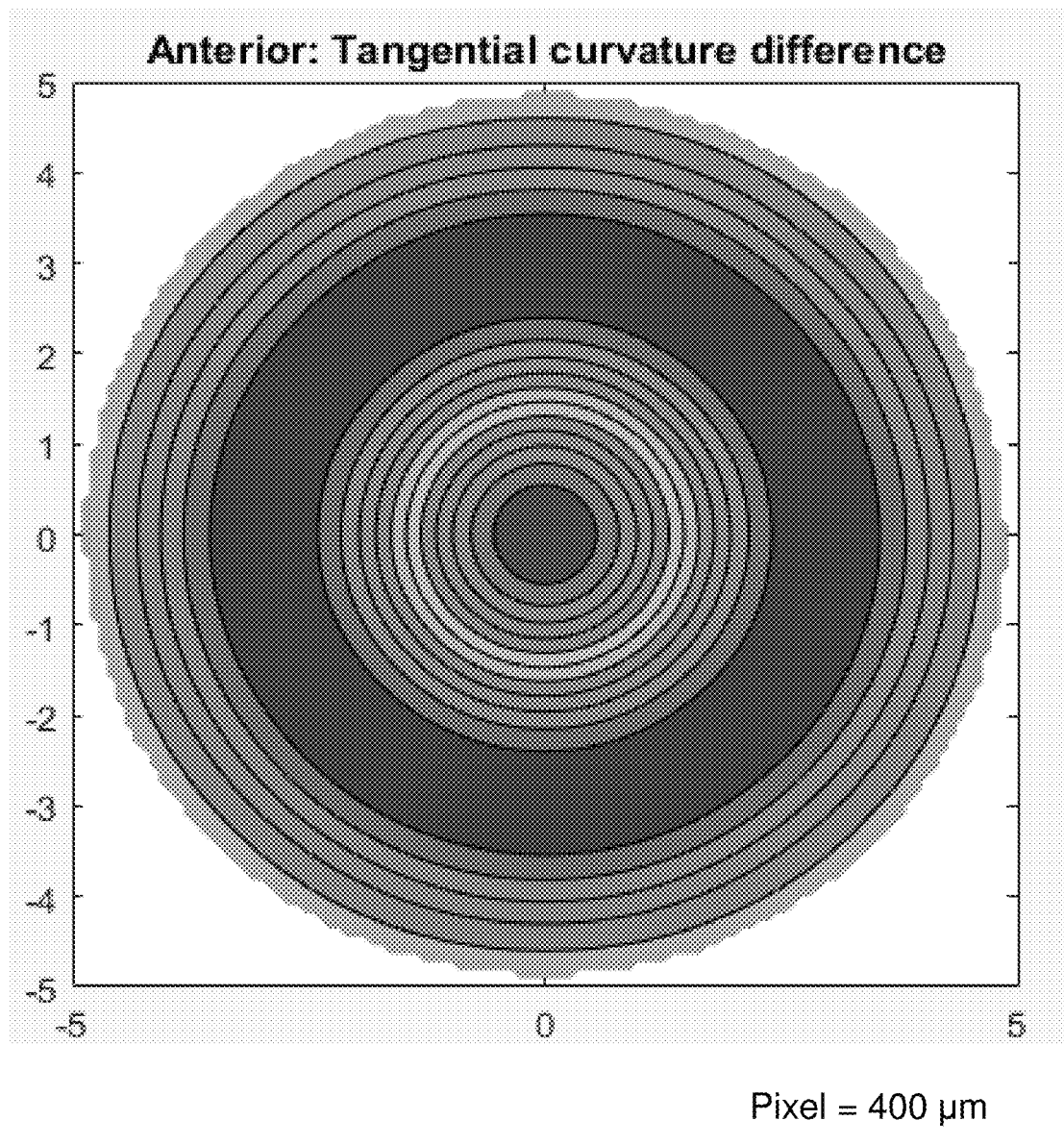
FIG. 8D illustrates modeled changes in tangential curvature of the anterior cornea following cross-linking treatments using the UV illumination pattern defined in FIG. 7D.
Figure 8E:
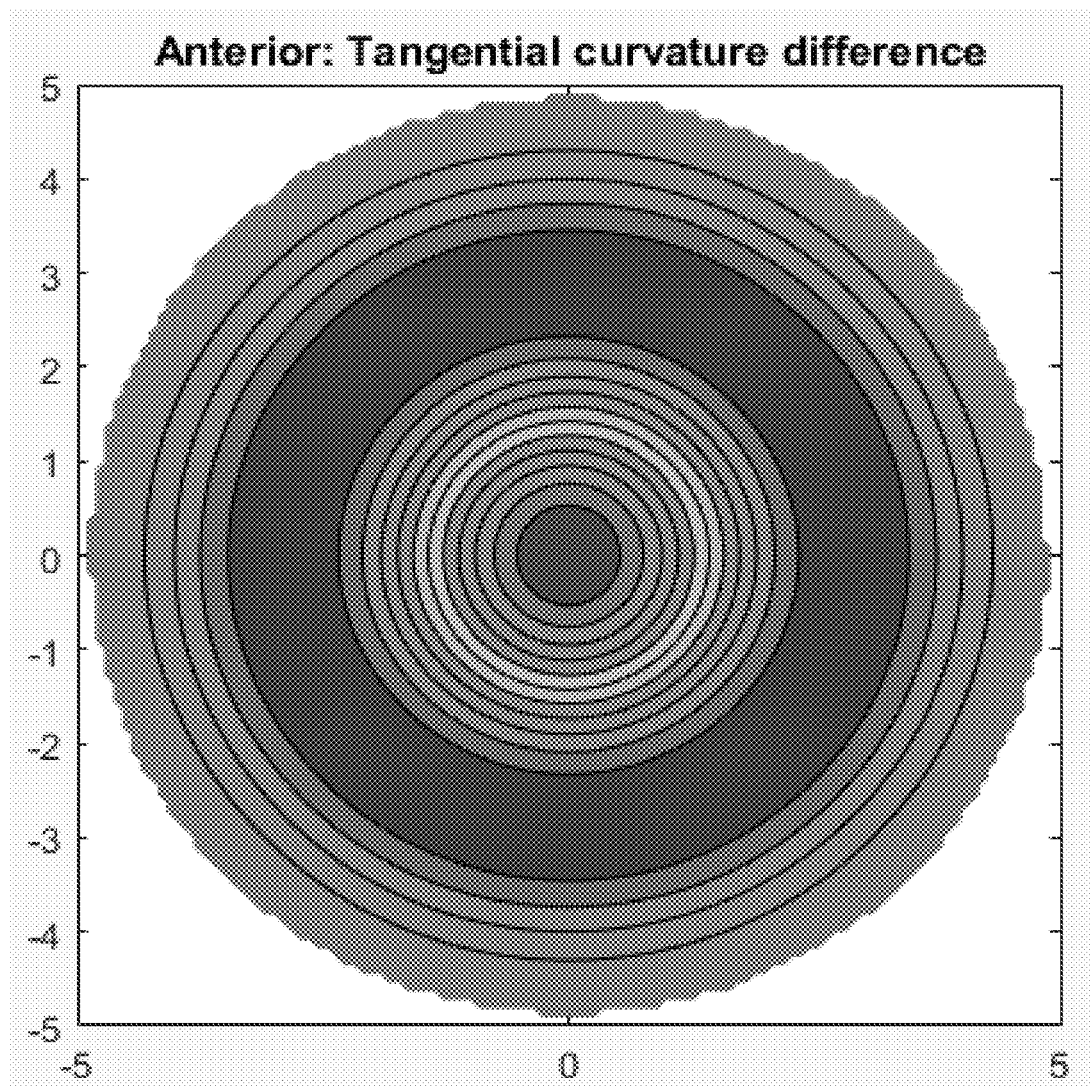
FIG. 8E illustrates modeled changes in tangential curvature of the anterior cornea following cross-linking treatments using the UV illumination pattern defined in FIG. 7E.
Figure 8F:
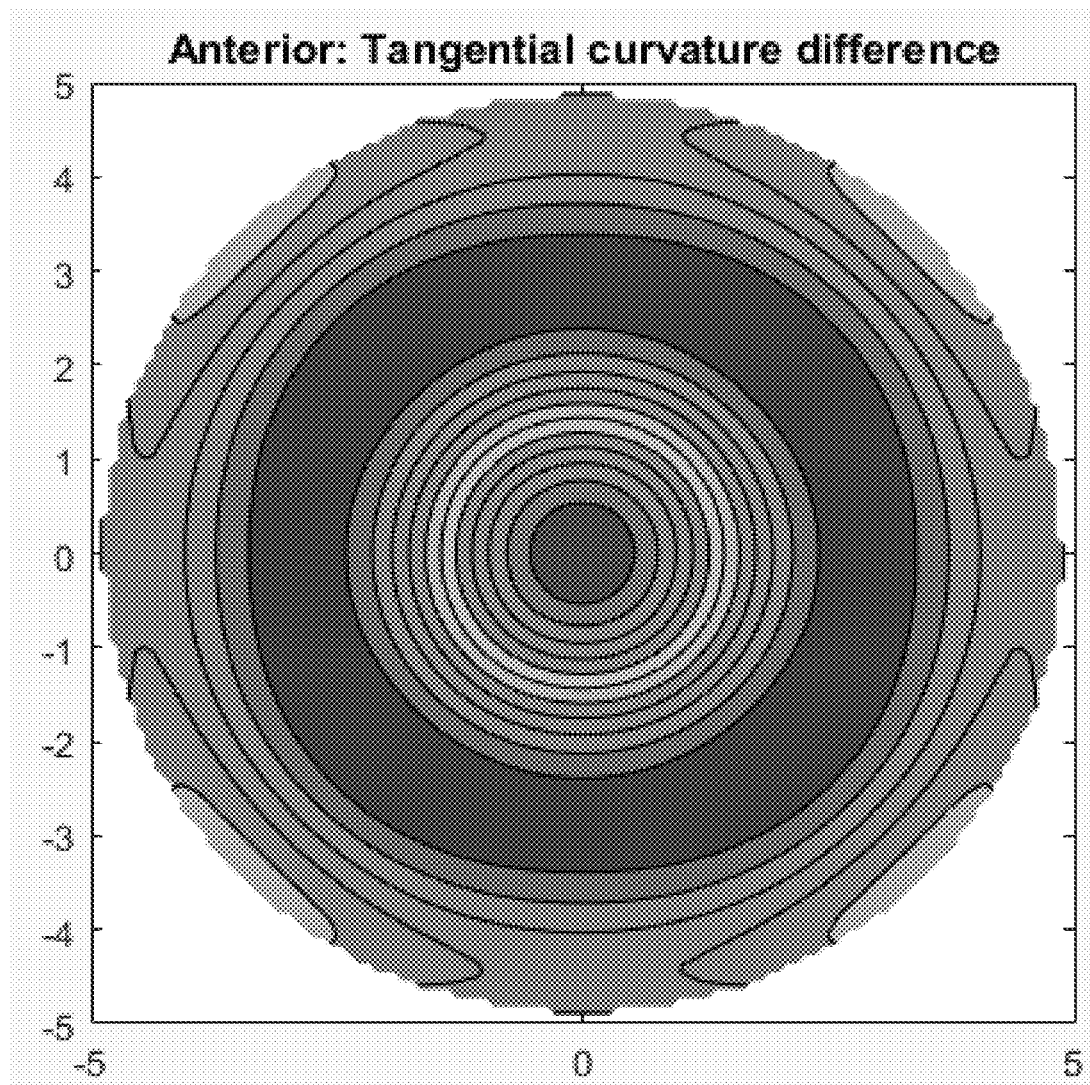
FIG. 8F illustrates modeled changes in tangential curvature of the anterior cornea following cross-linking treatments using the UV illumination pattern defined in FIG. 7F.

Correspondingly, FIGS. 8A-F illustrate modeled changes (from pre-treatment to post-treatment) in tangential curvature of the anterior cornea following cross-linking treatments using increasing pixel size for delivering the UV illumination pattern 706 as shown in FIGS. 7A-F, respectively. FIG. 8A illustrates the results when the illumination pattern 706 is defined by the pixels 708a (25 µm×25 µm). FIG. 8B illustrates the results when the illumination pattern 706 is defined by the pixels 708b (100 µm×100 µm). FIG. 8C illustrates the results when the illumination pattern 706 is defined by the pixels 708c (200 µm×200 µm). FIG. 8D illustrates the results when the illumination pattern 706 is defined by the pixels 708d (400 µm×400 µm). FIG. 8E illustrates the results when the illumination pattern 706 is defined by the pixels 708e (750 µm×750 µm). FIG. 8F illustrates the results when the illumination pattern 706 is defined by the pixels 708f (1000 µm×1000 µm). TABLE 1 illustrates the change in keratometry (D) over the central 3 mm area for various pixel sizes.

TABLE 1

| Pixel size, µm | Keratometry change, D |
| --- | --- |
| 10 | −1.62 |
| 25 | −1.62 |
| 50 | −1.62 |
| 250 | −1.62 |
| 400 | −1.61 |
| 500 | −1.60 |
| 750 | −1.61 |
| 1000 | −1.56 |
| 1500 | −1.47 |

Figure 9A:
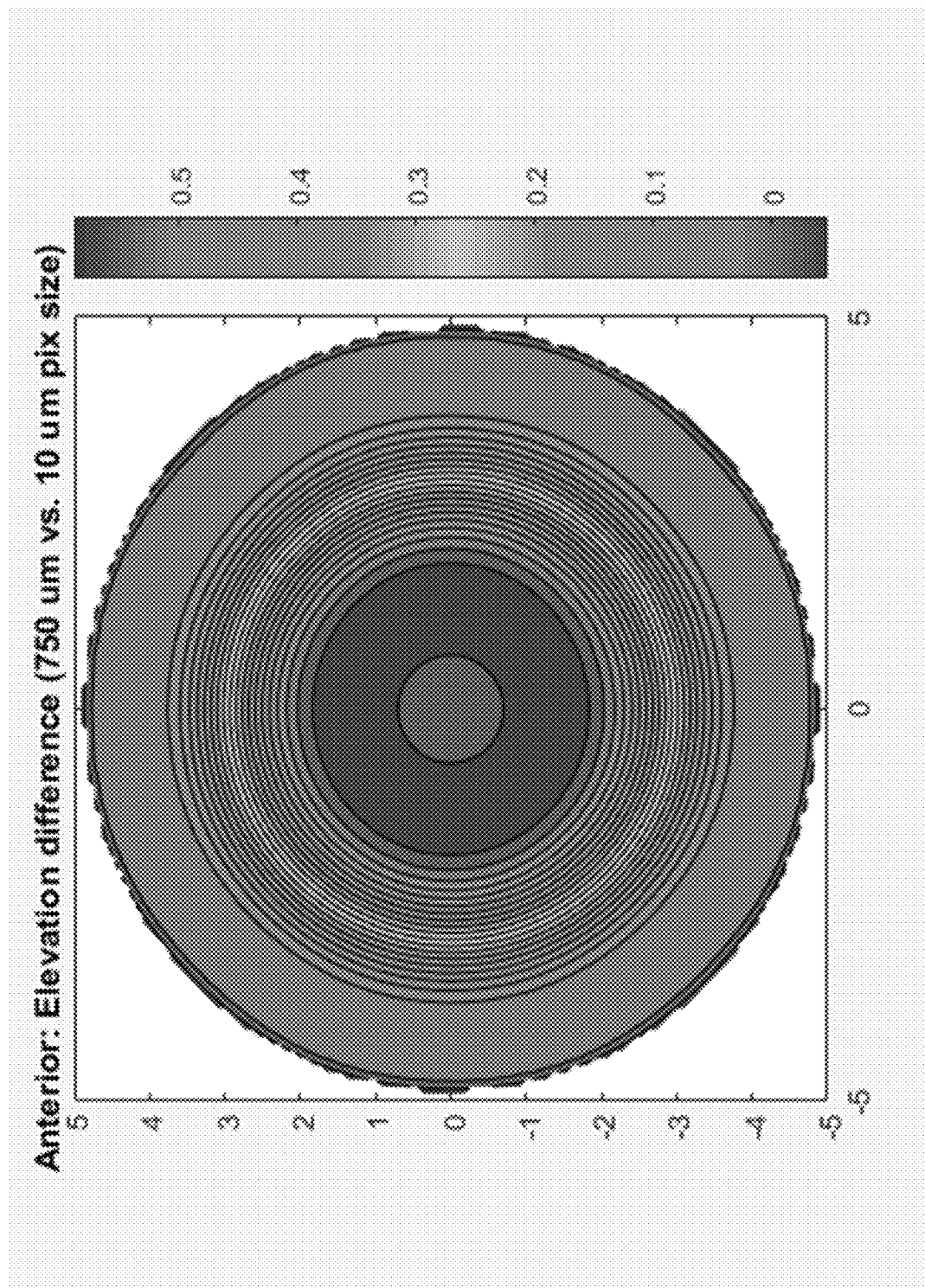
FIG. 9A illustrates a modeled difference in elevation (µm) of the anterior cornea between the results of two cross-linking treatments using a larger pixel (750 µm×750 µm) and a smaller pixel (10 µm×10 µm), respectively, for delivering a substantially circular UV illumination pattern, according to aspects of the present disclosure.
Figure 9B:
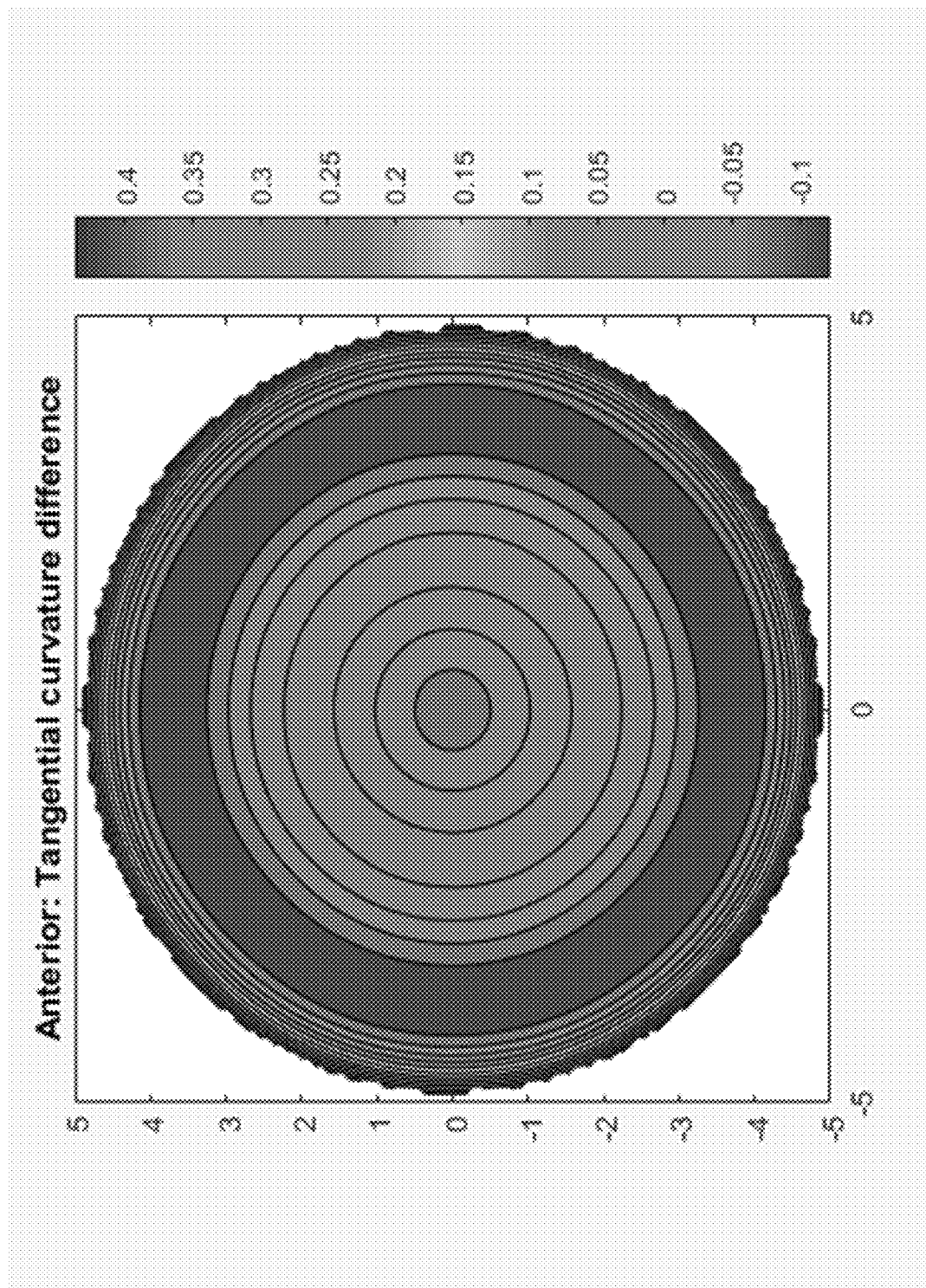
FIG. 9B illustrates a modeled difference in tangential curvature (D) of the anterior cornea between the results of the two cross-linking treatments of FIG. 9A.

FIGS. 9A-B illustrate a modeled difference between the results of two cross-linking treatments using a larger pixel and a smaller pixel, respectively, for delivering a substantially circular UV illumination pattern. In particular, the larger pixel is 750 µm×750 µm in size, and the smaller pixel is 10 µm×10 µm in size. FIG. 9A illustrates the resulting elevation (µm) of the anterior cornea after using the larger pixel minus the resulting elevation (µm) in the anterior cornea after using the smaller pixel. FIG. 9B illustrates the resulting tangential curvature (D) of the anterior cornea after using the larger pixel minus the tangential curvature (D) of the anterior cornea after using the smaller pixel.

As the results of 8A-F and TABLE 1 demonstrate, however, the changes in tangential curvature and keratometry are effectively similar for treatments using pixel sizes of up to 250 µm×250 µm, or even 400 µm×400 µm, for substantially circular illumination patterns. The similar results of the larger pixel sizes (e.g., compared to smaller 10 µm×10 µm pixels) allow effective implementation of the eye tracking approach of the example system 300 described above.

Figure 10A:
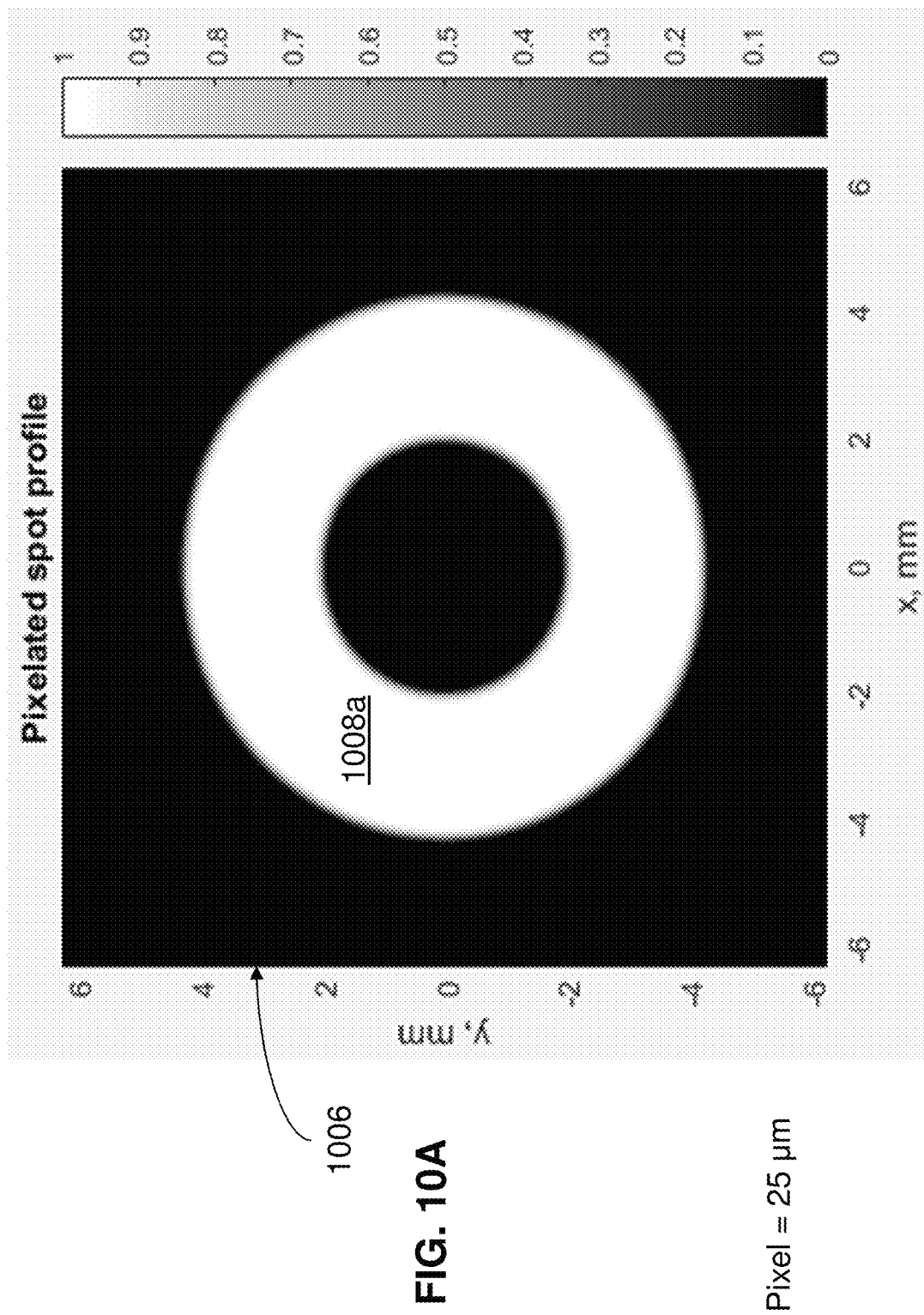
FIG. 10A illustrates a substantially annular UV illumination pattern (inner diameter=4 mm, outer diameter=8.5 mm) defined by pixels that are 25 µm×25 µm in size, according to aspects of the present disclosure.
Figure 10B:
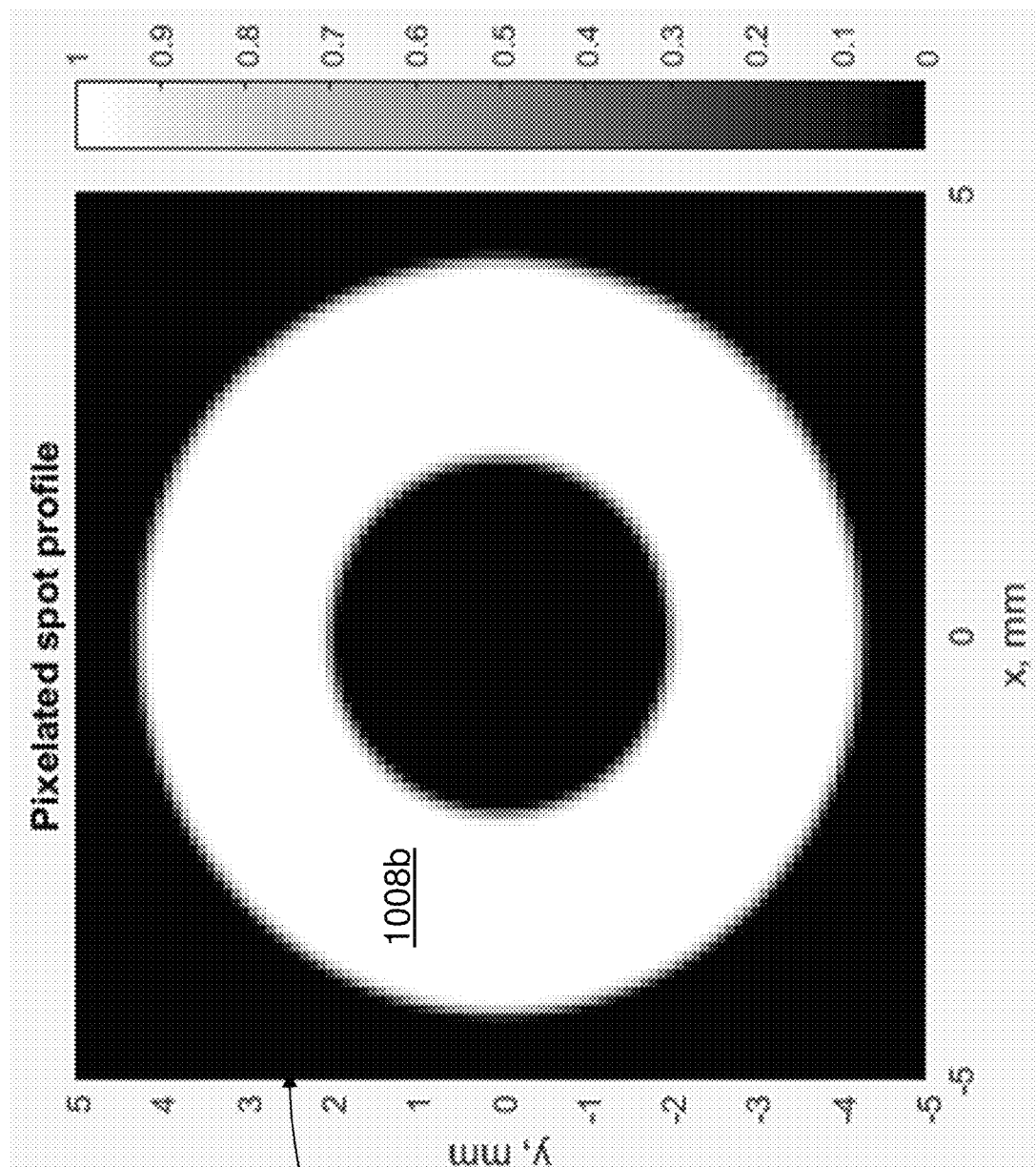
FIG. 10B illustrates a substantially annular UV illumination pattern (inner diameter=4 mm, outer diameter=8.5 mm) defined by pixels that are 100 µm×100 µm in size, according to aspects of the present disclosure.
Figure 10C:
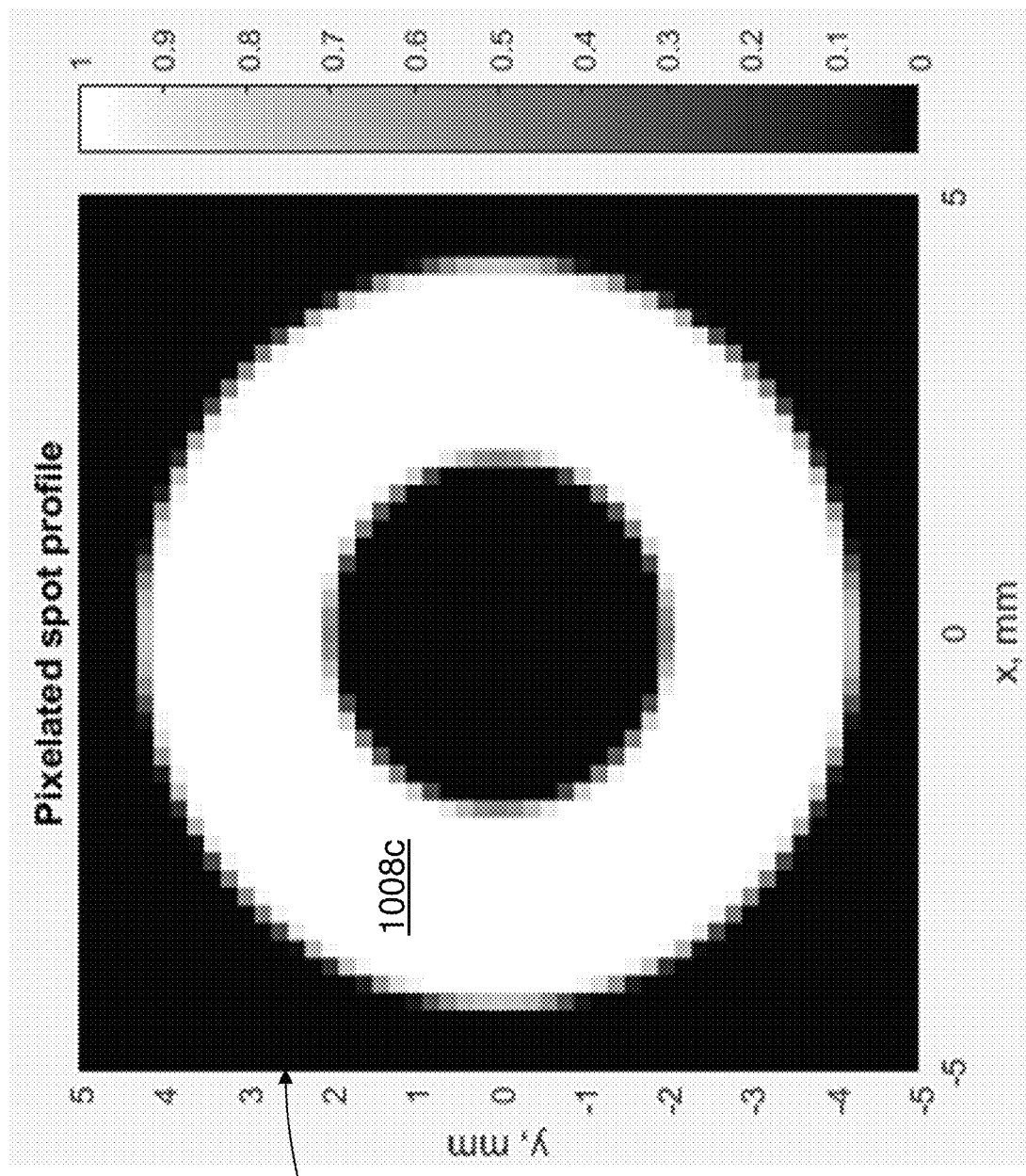
FIG. 10C illustrates a substantially annular UV illumination pattern (inner diameter=4 mm, outer diameter=8.5 mm) defined by pixels that are 200 µm×200 µm in size, according to aspects of the present disclosure.
Figure 10D:
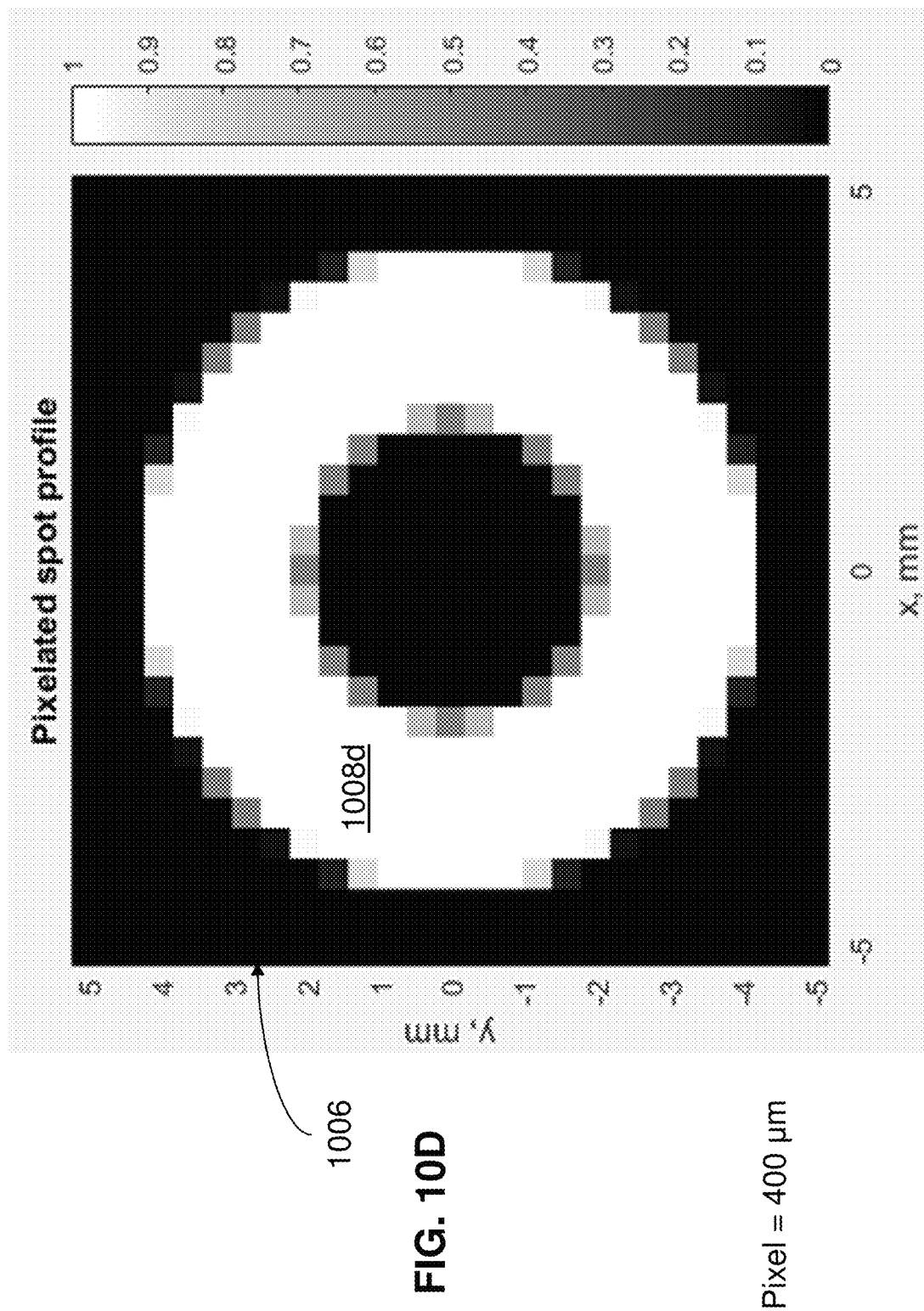
FIG. 10D illustrates a substantially annular UV illumination pattern (inner diameter=4 mm, outer diameter=8.5 mm) defined by pixels that are 400 µm×400 µm in size, according to aspects of the present disclosure.
Figure 10E:
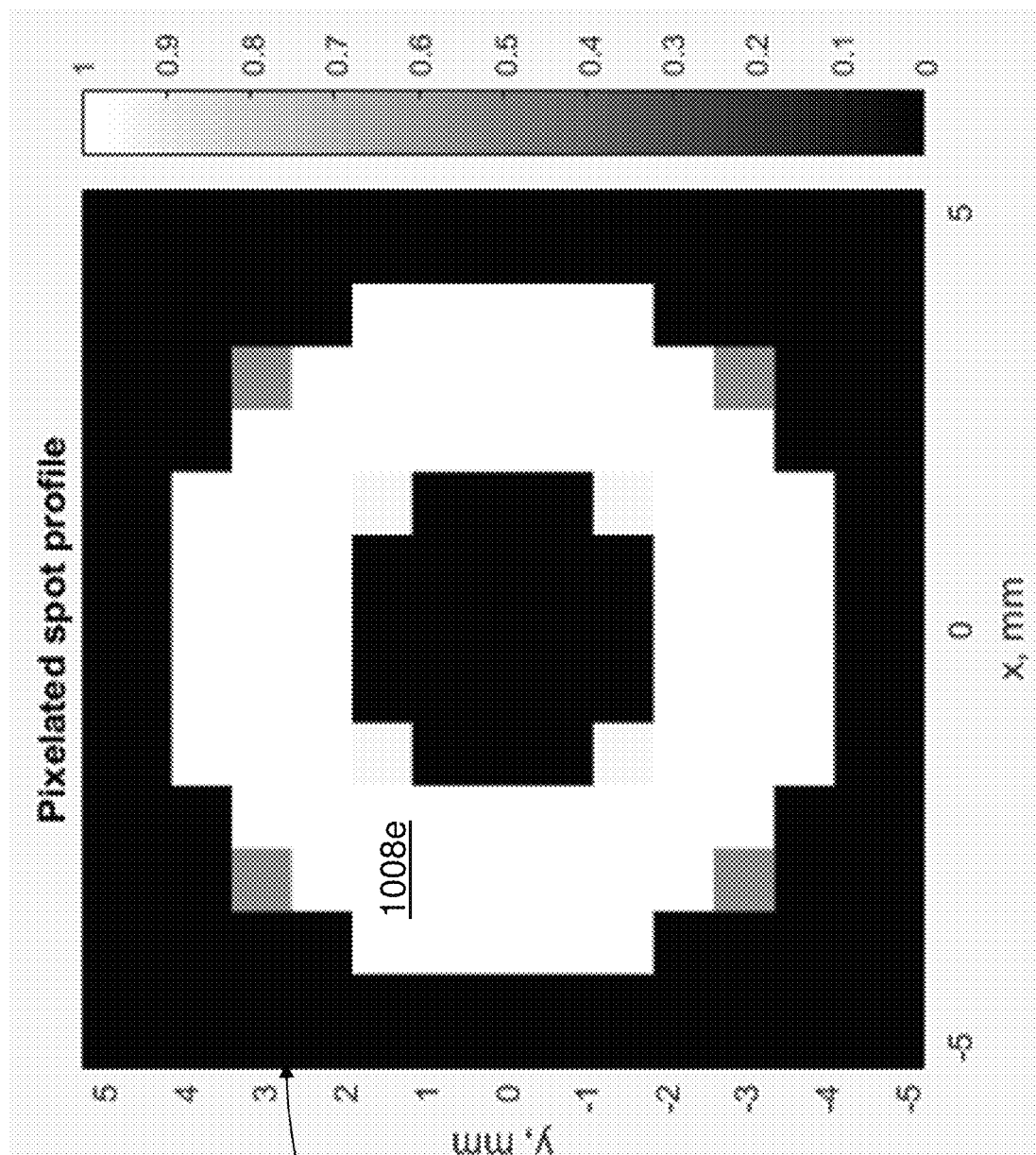
FIG. 10E illustrates a substantially annular UV illumination pattern (inner diameter=4 mm, outer diameter=8.5 mm) defined by pixels that are 750 µm×750 µm in size, according to aspects of the present disclosure.
Figure 10F:
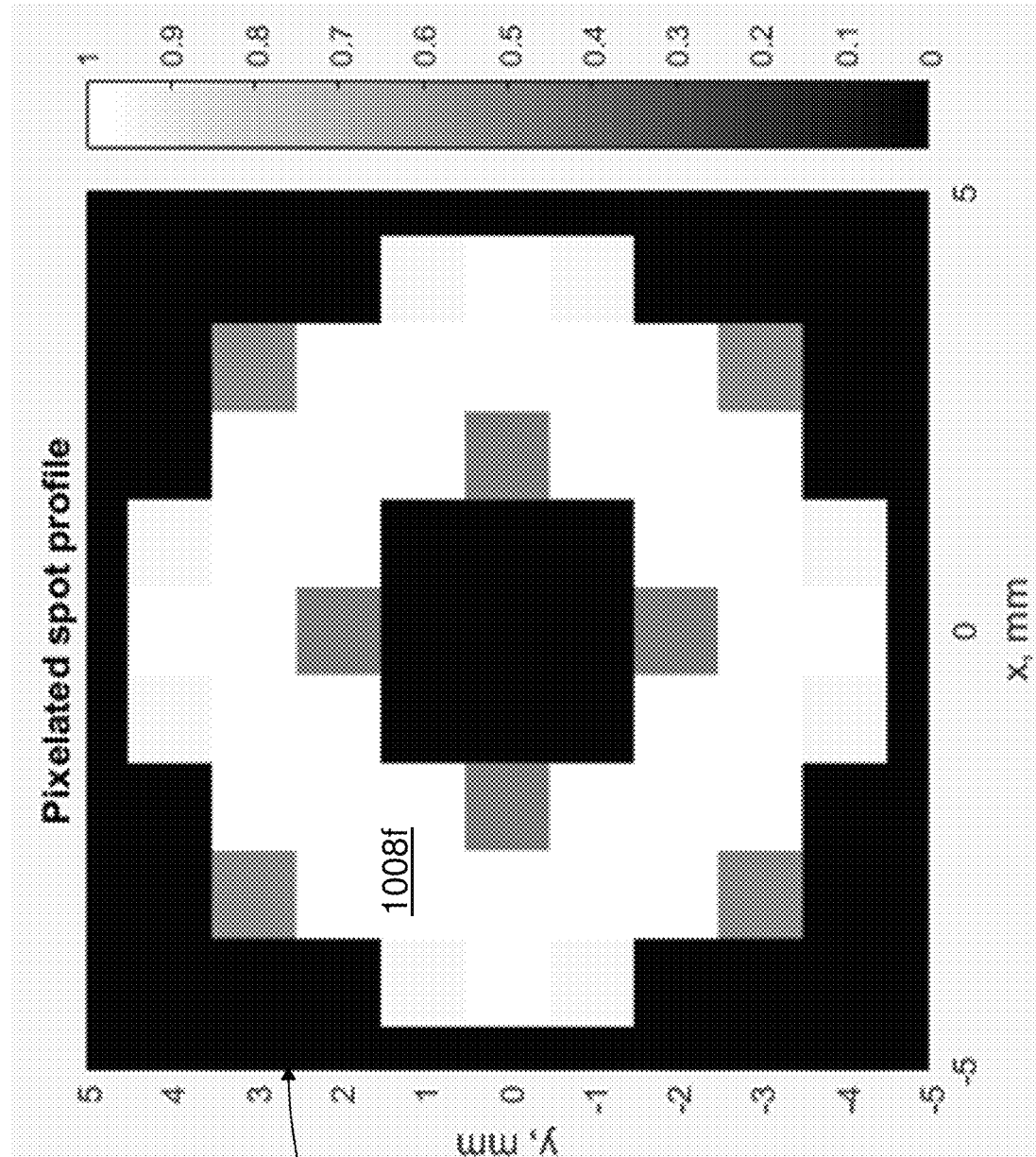
FIG. 10F illustrates a substantially annular UV illumination pattern (inner diameter=4 mm, outer diameter=8.5 mm) defined by pixels that are 1000 µm×1000 µm in size, according to aspects of the present disclosure.

FIGS. 10A-F illustrate the use of increasing pixel size for delivering a substantially annular UV illumination pattern 1006. The illumination pattern 1006 has an inner diameter of approximately 4 mm and an outer diameter of approximately 8.5 mm. The illumination pattern 1006 may be employed, for instance, to generate a corresponding area of cross-linking activity in the cornea to treat hyperopia or presbyopia. In FIG. 10A, the illumination pattern 1006 is defined by pixels 1008a, which are 25 µm×25 µm in size. In FIG. 10B, the illumination pattern 1006 is defined by pixels 1008b, which are 100 µm×100 µm in size. In FIG. 10C, the illumination pattern 1006 is defined by pixels 1008c, which are 200 µm×200 µm in size. In FIG. 10D, the illumination pattern 1006 is defined by pixels 1008d, which are 400 µm×400 µm in size. In FIG. 10E, the illumination pattern 1006 is defined by pixels 1008e, which are 750 µm×750 µm in size. In FIG. 10F, the illumination pattern 1006 is defined by pixels 1008f, which are 1000 µm×1000 µm in size. The effects of eye motion on the illumination pattern 1006 are modeled in FIGS. 10A-F with a 100 µm blurring function along the edge of the illumination pattern 1006.

Figure 11A:
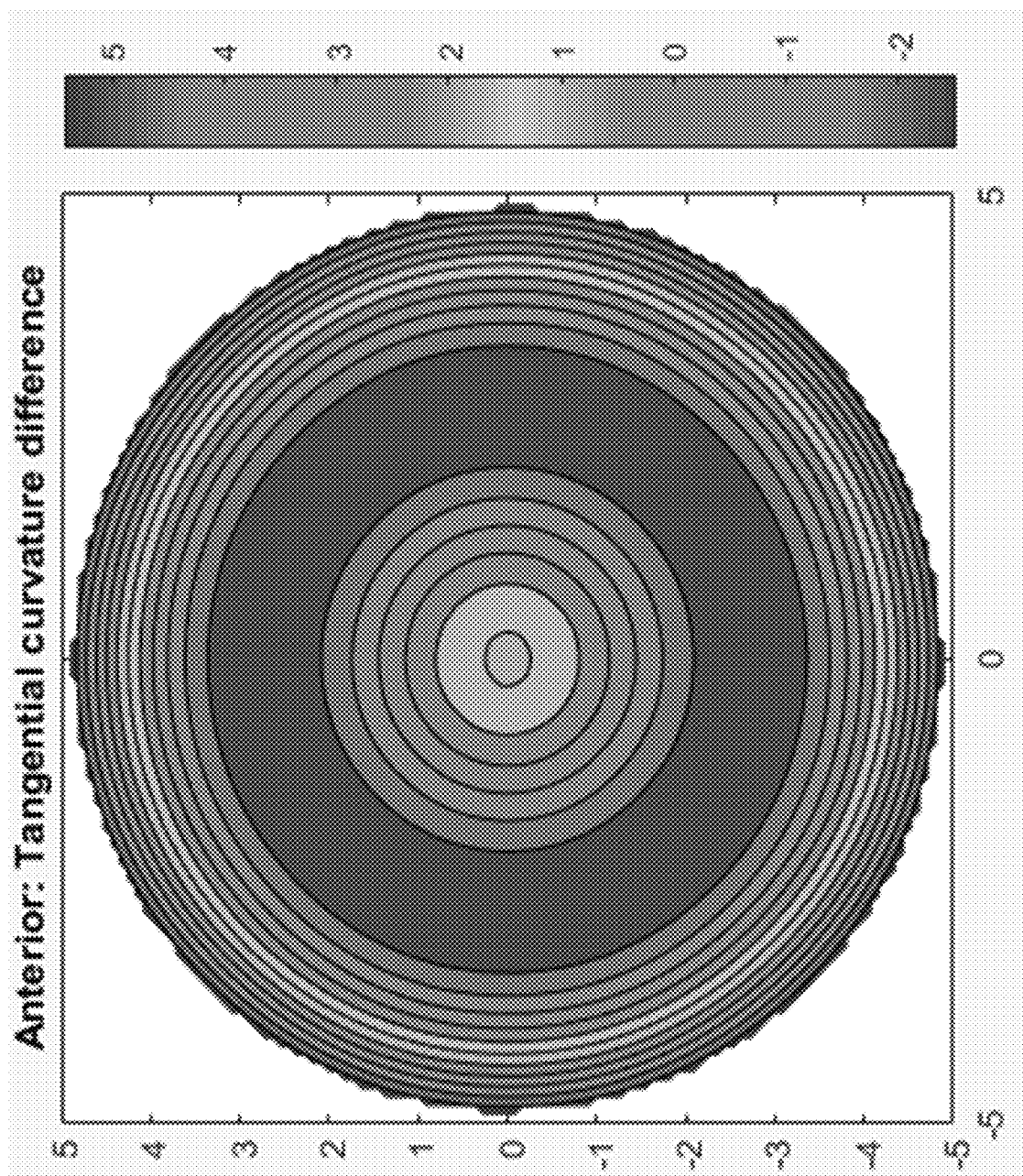
FIG. 11A illustrates modeled changes in tangential curvature of the anterior cornea following cross-linking treatments using the UV illumination pattern defined in FIG. 10A.
Figure 11B:
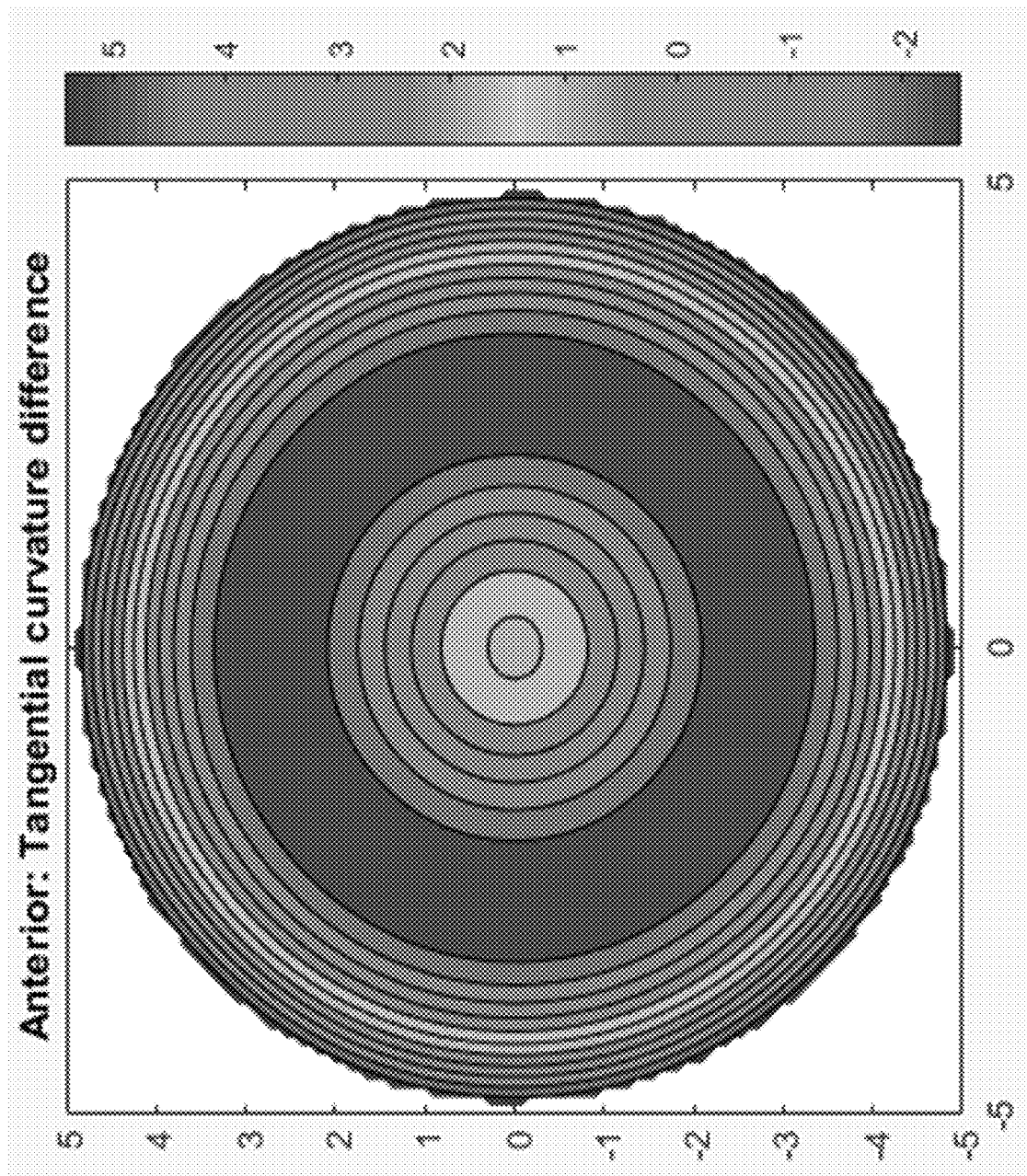
FIG. 11B illustrates modeled changes in tangential curvature of the anterior cornea following cross-linking treatments using the UV illumination pattern defined in FIG. 10B.
Figure 11C:
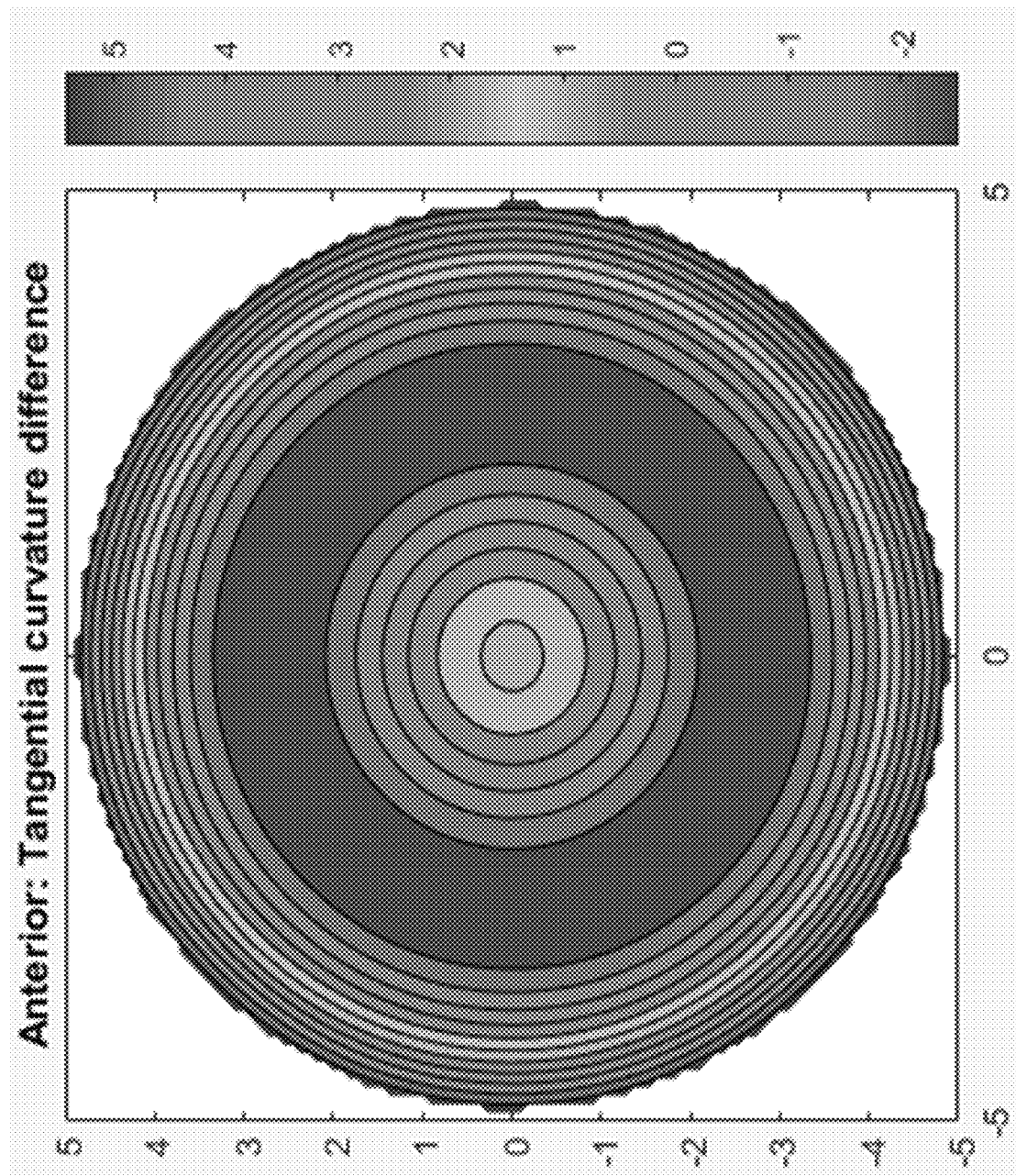
FIG. 11C illustrates modeled changes in tangential curvature of the anterior cornea following cross-linking treatments using the UV illumination pattern defined in FIG. 10C.
Figure 11D:
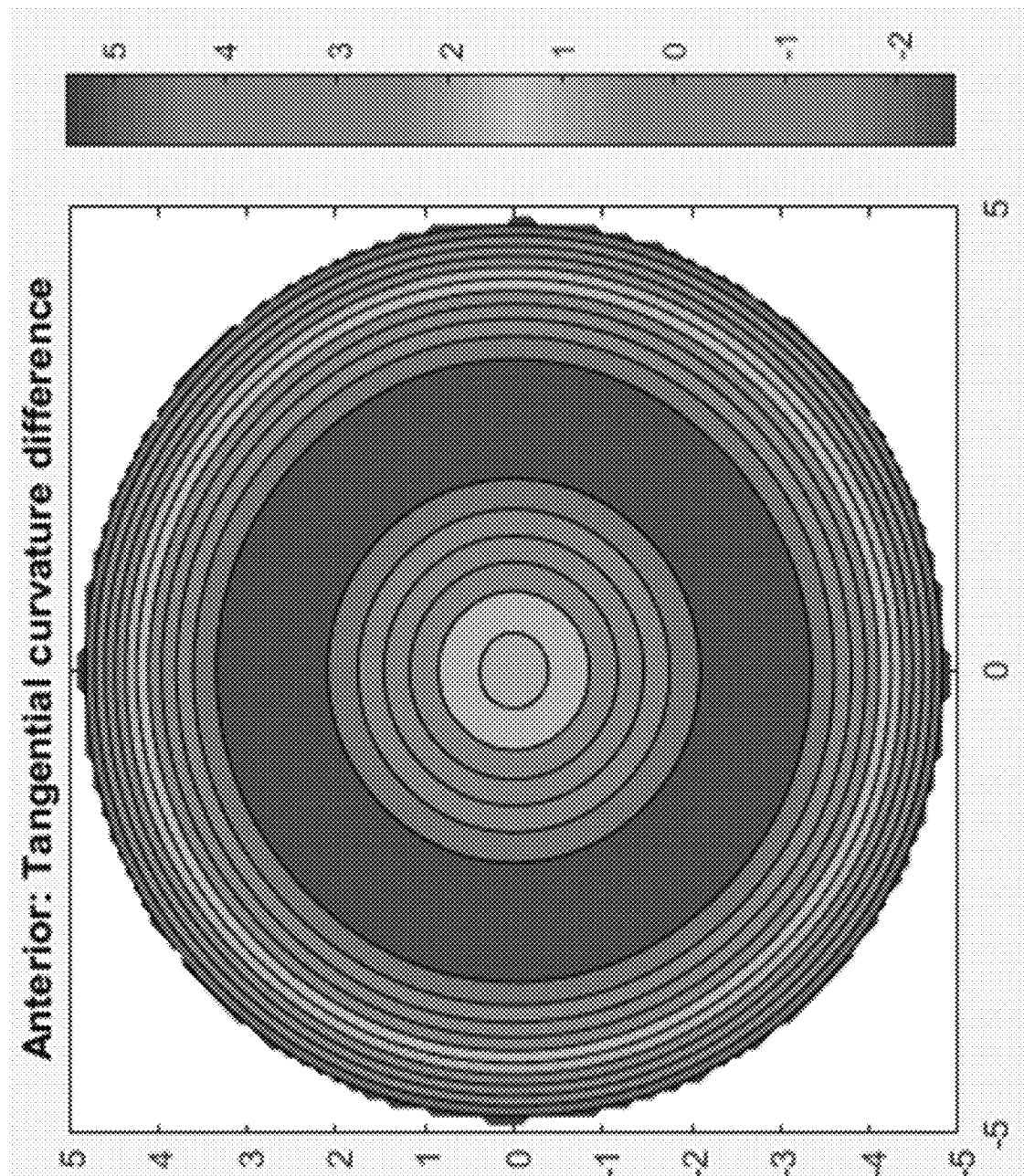
FIG. 11D illustrates modeled changes in tangential curvature of the anterior cornea following cross-linking treatments using the UV illumination pattern defined in FIG. 10D.
Figure 11E:
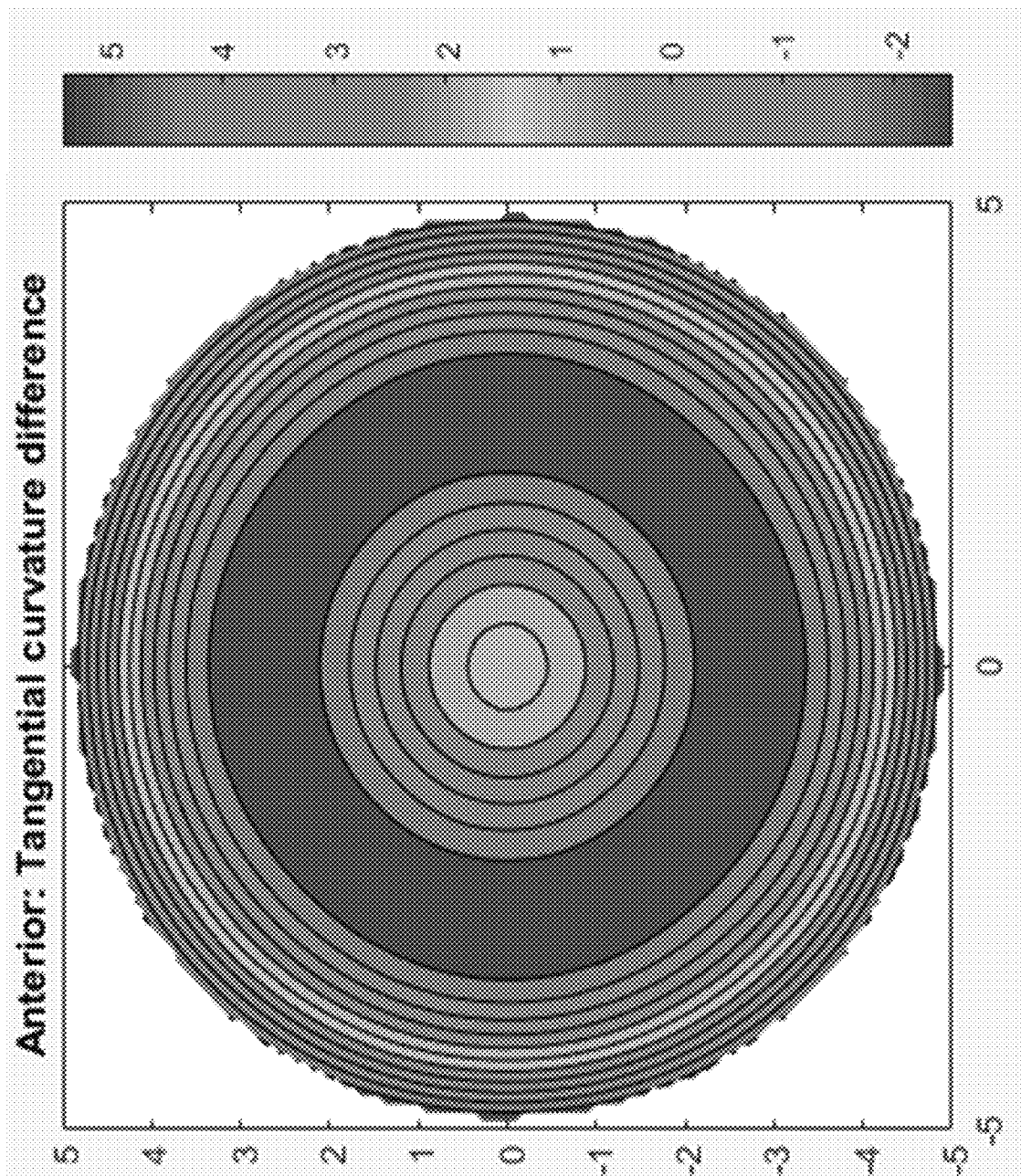
FIG. 11E illustrates modeled changes in tangential curvature of the anterior cornea following cross-linking treatments using the UV illumination pattern defined in FIG. 10E.
Figure 11F:
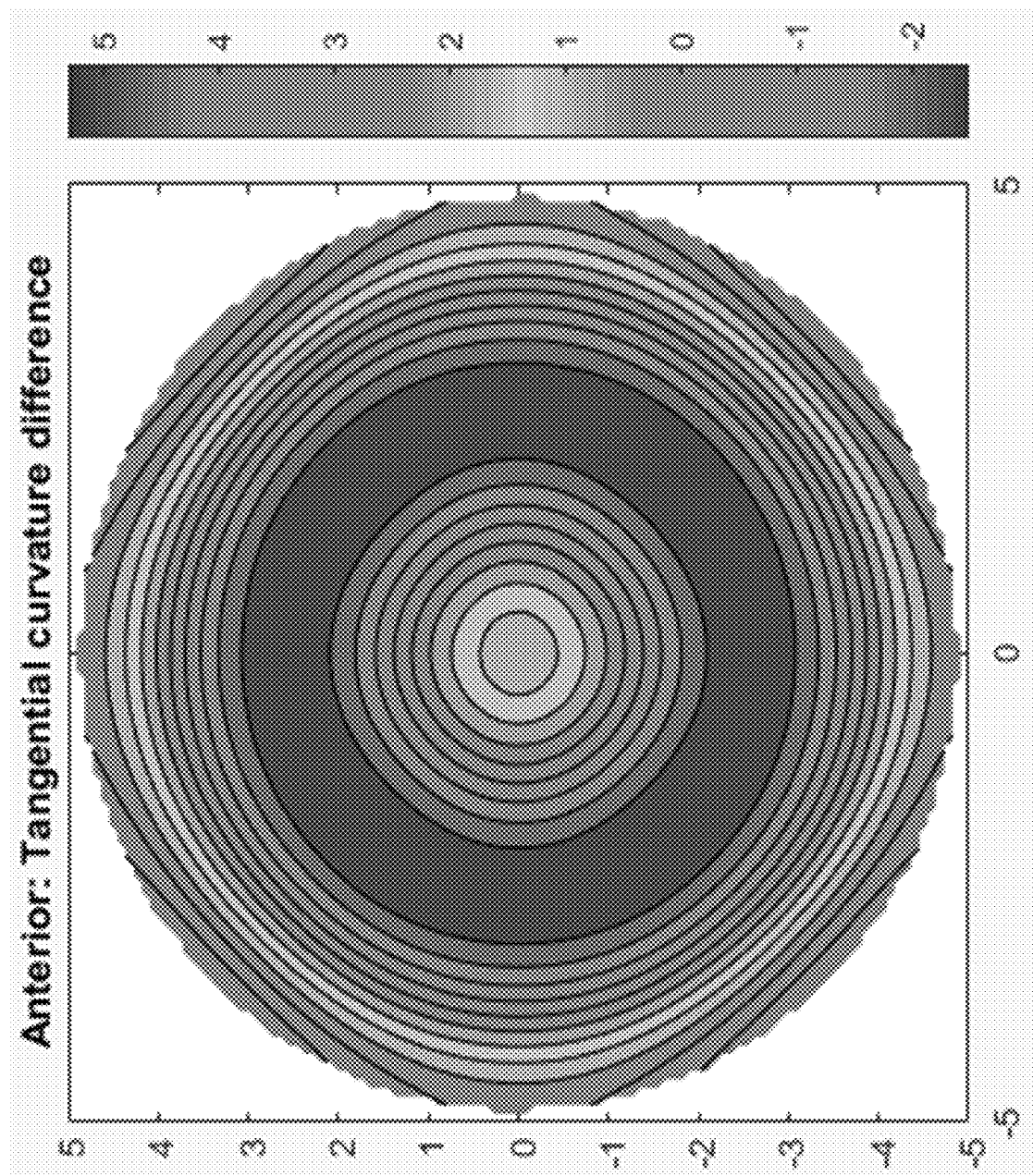
FIG. 11F illustrates modeled changes in tangential curvature of the anterior cornea following cross-linking treatments using the UV illumination pattern defined in FIG. 10F.

Correspondingly, FIGS. 11A-F illustrate modeled changes (from pre-treatment to post-treatment) in tangential curvature of the anterior cornea following cross-linking treatments using increasing pixel size for delivering the UV illumination pattern 1006 as shown in FIGS. 10A-F, respectively. FIG. 11A illustrates the results when the illumination pattern 1006 is defined by the pixels 1008a (25 µm×25 µm). FIG. 11B illustrates the results when the illumination pattern 1006 is defined by the pixels 1008b (100 µm×100 µm). FIG. 11C illustrates the results when the illumination pattern 1006 is defined by the pixels 1008c (200 µm×200 µm). FIG. 11D illustrates the results when the illumination pattern 1006 is defined by the pixels 1008*d* (400 µm×400 µm). FIG. 11E illustrates the results when the illumination pattern 1006 is defined by the pixels 1008*e* (750 µm×750 µm). FIG. 11F illustrates the results when the illumination pattern 1006 is defined by the pixels 1008*f* (1000 µm×1000 µm). TABLE 2 illustrates the change in keratometry (D) over the central 3 mm area for various pixel sizes.

TABLE 2

| Pixel size, µm | Keratometry change, D |
|---|---|
| 10 | 1.09 |
| 200 | 1.09 |
| 400 | 1.07 |
| 750 | 1.03 |
| 1000 | 1.01 |
| 1500 | 0.87 |

Figure 12A:
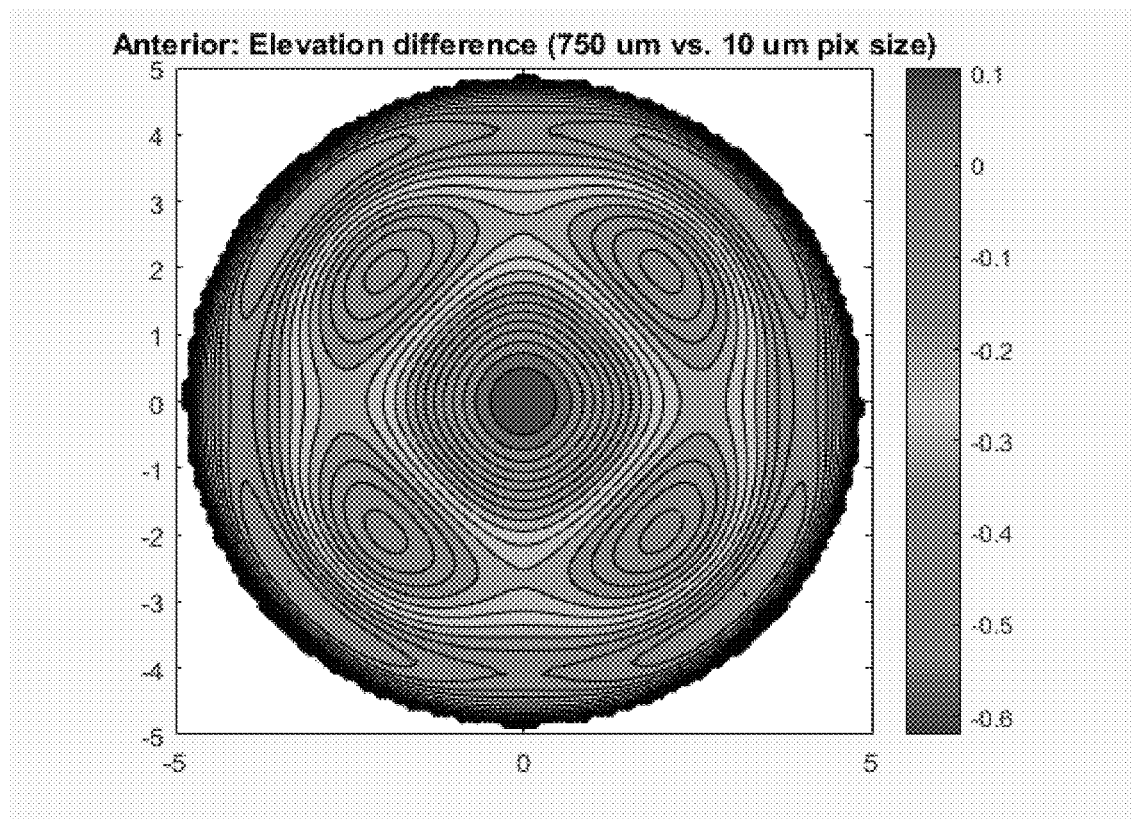
FIG. 12A illustrates a modeled difference in elevation (µm) of the anterior cornea between the results of two cross-linking treatments using a larger pixel (750 µm×750 µm) and a smaller pixel (10 µm×10 µm), respectively, for delivering a substantially annular UV illumination pattern, according to aspects of the present disclosure.
Figure 12B:
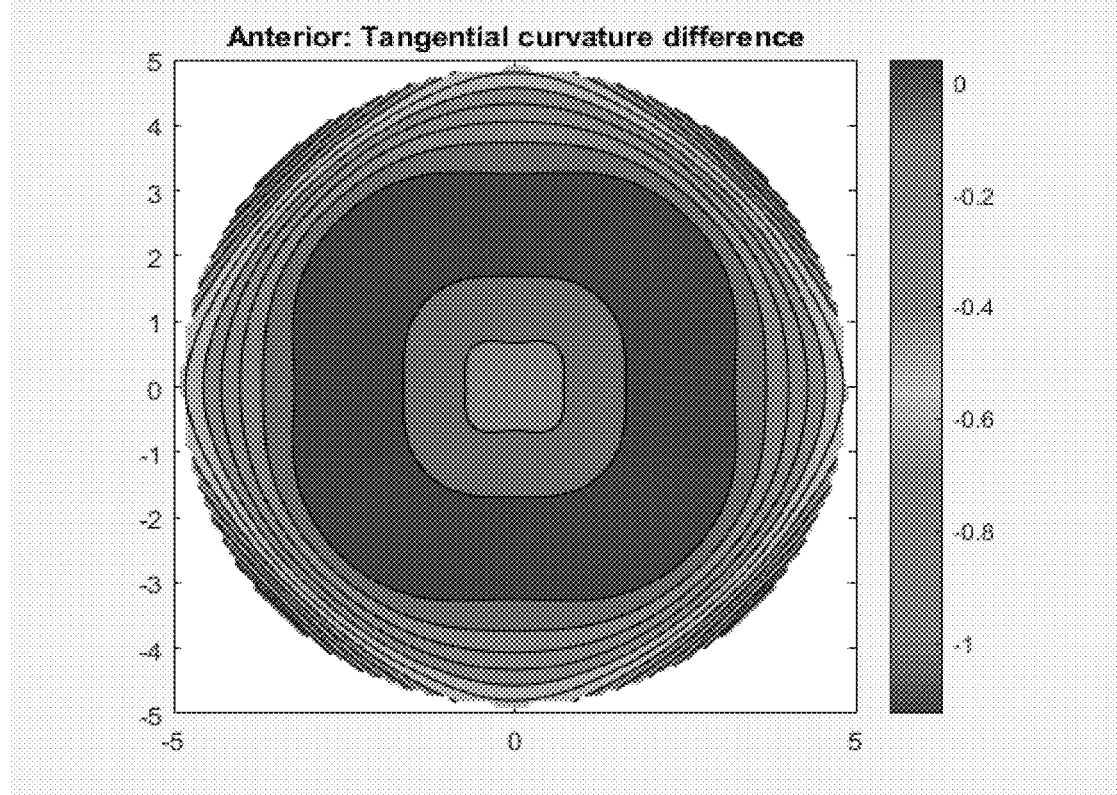
FIG. 12B illustrates a modeled difference in tangential curvature (D) of the anterior cornea between the results of the two cross-linking treatments of FIG. 12A.

FIGS. 12A-B illustrate a modeled difference between the results of two cross-linking treatments using a larger pixel and a smaller pixel, respectively, for delivering a substantially annular UV illumination pattern. In particular, the larger pixel is 750 µm×750 µm in size, and the smaller pixel is 10 µm×10 µm in size. FIG. 12A illustrates the resulting elevation (µm) of the anterior cornea after using the larger pixel minus the resulting elevation (µm) in the anterior cornea after using the smaller pixel. FIG. 12B illustrates the resulting tangential curvature (D) of the anterior cornea after using the larger pixel minus the tangential curvature (D) of the anterior cornea after using the smaller pixel.

As the results of 11A-F and TABLE 2 demonstrate, however, the changes in tangential curvature and keratometry are effectively similar for treatments using pixel sizes of up to 200 µm×200 µm, or even 400 µm×400 µm, for substantially annular illumination patterns. Again, the similar results of the larger pixel sizes (e.g., compared to smaller 10 µm×10 µm pixels) allow effective implementation of the eye tracking approach of the example system 300 described above.

Although the embodiments above may involve the use of a DMD device, other embodiments may employ any type of programmable spatial light modulator to achieve similar results. For instance, embodiments may employ a liquid crystal microdisplay, which is transmissive or reflective. Spatial light modulators that impart a polarization change can be used in conjunction with a fixed polarizer to achieve similar results. Transmissive implementations may also have additional advantages with respect to overall system size.

In view of the foregoing, embodiments employ a purely digital means for eye tracking that can be used with an illumination system to perform corneal cross-linking. In particular, the embodiments do not require electromechanical motion systems (e.g., for adjustments along an x-y plane) to keep the beam photoactivating light aligned with desired area of the subject's eye. Advantageously, this allows the cost and complexity of treatment systems to be significantly reduced. Additionally, among other advantages, the system allows for increased response time relative to other systems, adjustments to rotational movement of the eye, and compensation for geometric distortions caused by change in eye gaze angle and/or head movement.

As described above, according to some aspects of the present disclosure, some or all of the steps of the above-described and illustrated procedures can be automated or guided under the control of a controller (e.g., the controller 120). Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the example embodiments of the present disclosure, as is appreciated by those skilled in the computer and software arts. The physical processors and/or machines may be externally networked with image capture device(s) (e.g., the camera 252), or may be integrated to reside within the image capture device. Appropriate software can be readily prepared by programmers of ordinary skill based on the teachings of the example embodiments, as is appreciated by those skilled in the software art. In addition, the devices and subsystems of the example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of computer readable media, the example embodiments of the present disclosure may include software for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the example embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the present disclosure. It is also contemplated that additional embodiments according to aspects of the present disclosure may combine any number of features from any of the embodiments described herein.

What is claimed is:

1. A system for applying a cross-linking treatment to a cornea of an eye, comprising:
   a light source configured to emit a photoactivating light;
   a spatial light modulator configured to receive the photoactivating light from the light source and provide a pixelated illumination with the photoactivating light; and
   a controller configured to cause the spatial light modulator to project a first pixelated illumination and a second pixelated illumination onto a cornea to generate cross-linking activity in a desired treatment area by photoactivating a cross-linking agent applied to the desired treatment area, the desired treatment area including at least one portion that is not illuminated by the first pixelated illumination, the second pixelated illumination including one or more pixels that illuminate the at least one portion of the desired treatment area that is not illuminated by the first pixelated illumination, the first pixelated illumination is projected inside the desired treatment area, and the one or more pixels of the second pixelated illumination is projected inside and outside the desired treatment area, the spatial light modulator projecting the first pixelated illumination and the second pixelated illumination to the cornea according to different temporal spatial and temporal irradiance and dose profiles.

2. The system of claim 1, wherein the first pixelated illumination includes all complete pixels that can be projected within the desired treatment area, and the one or more pixels of the second pixelated illumination includes remaining pixels that, in combination with the pixels of the first pixelated illumination, illuminate the entire desired treatment area.

3. The system of claim 1, wherein the one or more pixels of the second pixelated illumination are positioned along a boundary of the desired treatment area.

4. The system of claim 1, wherein the first pixelated illumination is projected onto the cornea for a duration and the second pixelated illumination is dithered onto the cornea at a rapid rate during the duration.

5. The system of claim 1, wherein the first pixelated illumination is projected onto the cornea at every update cycle for the spatial light modulator and the second pixelated illumination is projected onto the cornea at alternating update cycles.

6. The system of claim 1, wherein the controller is configured to cause the spatial light modulator to project one or more additional pixelated illuminations onto the cornea, the additional pixelated illuminations illuminate other respective portions of the desired treatment area that are not illuminated by the first pixelated illumination, and the spatial light modulator projects the first pixelated illumination, the second pixelated illumination, and the one or more additional pixelated illuminations according to different temporal spatial and temporal irradiance and dose profiles.

7. The system of claim 1, wherein the first pixelated illumination and the second pixelated illumination are projected onto a plane defined by two axes, the first pixelated illumination and the second pixelated illumination have same shape and size, and the first pixelated illumination and the second pixelated illumination are spatially offset along at least one of the two axes.

8. The system of claim 7, wherein the controller is configured to cause the spatial light modulator to further project a third pixelated illumination and fourth pixelated illumination,
   the first pixelated illumination, the second pixelated illumination, the third pixelated illumination, and the fourth pixelated illumination have same shape and size,
   the first pixelated illumination, the second pixelated illumination, the third pixelated illumination, and the fourth pixelated illumination are spatially offset from each other along at least one of the two axes, and
   the first pixelated illumination, the second pixelated illumination, the third pixelated illumination, and the fourth pixelated illumination are alternately projected onto the cornea to collectively illuminate the entire desired treatment area.

9. The system of claim 1, wherein the spatial light modulator is a DMD, the DMD including a plurality of mirrors arranged in a array, the plurality of mirrors configured to selectively reflect the photoactivating light from the light source to provide the pixelated illumination.

10. The system of claim 1, wherein the controller is further configured to determine movement of the cornea, and in response to the movement, the controller controls the spatial light modulator to at least one of translate or transform the first pixelated illumination to illumination to continue photoactivating the cross-linking agent applied to the desired treatment area.

* * * * *

UNITED STATES PATENT AND TRADEMARK OFFICE
CERTIFICATE OF CORRECTION

PATENT NO. : 12,042,433 B2
APPLICATION NO. : 16/978694
DATED : July 23, 2024
INVENTOR(S) : Desmond Christopher Adler, David Usher and Mikhail Smirnov It is certified that error appears in the above-identified patent and that said Letters Patent is hereby corrected as shown below:

In the Claims

Column 17, Line 36 (Claim 1) replace "temporal spatial" with --spatial--.

Column 18, Line 15 (Claim 6) replace "temporal spatial" with --spatial--.

Signed and Sealed this
Fourth Day of November, 2025

John A. Squires
*Director of the United States Patent and Trademark Office*